US011673912B2

(12) United States Patent
Yeboue et al.

(10) Patent No.: US 11,673,912 B2
(45) Date of Patent: Jun. 13, 2023

(54) CONTINUOUS, SOLVENT-FREE AND NON-ENZYMATIC PEPTIDE SYNTHESIS BY REACTIVE EXTRUSION

(71) Applicants: CENTRE NATIONAL DE LA RECHERCHE SCIENTIFIQUE, Paris (FR); UNIVERSITE DE MONTPELLIER, Montpellier (FR); ECOLE NATIONALE SUPERIEURE DE CHIMIE DE MONTPELLIER, Montpellier (FR); ECOLE DES MINES D'ALES, Ales (FR); ASSOCIATION POUR LA RECHERCHE ET LE DEVELOPPEMENT DES METHODES ET PROCESSUS INDUSTRIELS, Paris (FR)

(72) Inventors: Yves Yeboue, Montpellier (FR); Benjamin Gallard, Sarcelles (FR); Nicolas Le Moigne, Saint Sebastien d'Aigrefeuille (FR); Frédéric Lamaty, Montpellier (FR); Jean Martinez, Caux (FR); Thomas-Xavier Metro, Montpellier (FR)

(73) Assignees: CENTRE NATIONAL DE LA RECHERCHE SCIENTIFIQUE, Paris (FR); UNIVERSITE DE MONTPELLIER, Montpellier (FR); ECOLE NATIONALE SUPERIEURE DE CHIMIE DE MONTPELLIER, Montpellier (FR); ECOLE DES MINES D'ALES, Ales (FR); ASSOCIATION POUR LA RECHERCHE ET LE DEVELOPPEMENT DES METHODES ET PROCESSUS INDUSTRIELS, Paris (FR)

(*) Notice: Subject to any disclaimer, the term of this patent is extended or adjusted under 35 U.S.C. 154(b) by 32 days.

(21) Appl. No.: 16/970,435

(22) PCT Filed: Feb. 12, 2019

(86) PCT No.: PCT/EP2019/053389
§ 371 (c)(1),
(2) Date: Aug. 17, 2020

(87) PCT Pub. No.: WO2019/158506
PCT Pub. Date: Aug. 22, 2019

(65) Prior Publication Data
US 2021/0115085 A1 Apr. 22, 2021

(30) Foreign Application Priority Data

Feb. 16, 2018 (FR) .................. 18305160.6

(51) Int. Cl.
C07K 1/06 (2006.01)
B29C 48/395 (2019.01)
B29C 48/40 (2019.01)

(52) U.S. Cl.
CPC ............ *C07K 1/061* (2013.01); *B29C 48/397* (2019.02); *B29C 48/40* (2019.02); *B29K 2089/00* (2013.01)

(58) Field of Classification Search
CPC ...... C07K 1/061; C07K 1/063; B29C 48/397; B29C 48/40; B29K 2089/00
See application file for complete search history.

(56) References Cited

FOREIGN PATENT DOCUMENTS

WO 2008/125418 A2 10/2008

OTHER PUBLICATIONS

Hyvarinen et al, Polymers, 2020, 12, 1306, 1-14 (Year: 2020).*
Crawford, 2016, 28, 5747-5754 (Year: 2016).*
Declerck et al.; "Solvent-Free Synthesis of Peptides;" Angew. Chem. Int. Ed; 2009; pp. 9318-9321; vol. 48.
Hernández et al.; "Mechanoenzymatic peptide and amide bond formation;" Green Chem.; 2017; pp. 2620-2625; vol. 19, No. 11.
Ardila-Fierro et al.; "Papain-catalysed mechanochemical synthesis of oligopeptides by milling and twin-screw extrusion: application in the Julia-Colonna enantioselective epoxidation;" Green Chem.; 2018; pp. 1262-1269; vol. 20, No. 6.
Crawford et al.; "Organic synthesis by Twin Screw Extrusion (TSE): continuous, scalable and solvent-free;" Green Chem.; 2017; pp. 1507-1518; vol. 19, No. 6.
Apr. 12, 2019 Search Report issued in International Patent Application No. PCT/EP2019/053389.
Apr. 12, 2019 Written Opinion of the International Searching Authority issued in International Patent Application No. PCT/EP2019/053389.
Aug. 13, 2018 Extended Search Report issued in European Patent Application No. 18305160.6.

* cited by examiner

*Primary Examiner* — Sudhakar Katakam
(74) *Attorney, Agent, or Firm* — Oliff PLC

(57) ABSTRACT

A continuous, solvent-free and non-enzymatic method for synthesizing a compound of formula (I): Ra-POLYPEP-Rc (I) wherein: POLYPEP is a poly-amino acid compound, Ra and Rc are as specified, the method including the steps of: a) feeding an extrusion reactor with (1) a compound of formula (II) Ra-PEPNt-Rg (II) wherein; PEPNt is a mono- or a poly-amino acid compound, Ra and Rg are as specified, and (2) a compound of formula (III) H-PEPCt-Rc (III) wherein: PEPCt is a mono- or a poly-amino acid compound, and Rc is as defined in the absence of any solvent, so that the compound of formula (II) and the compound of formula (III) react together for generating a compound of formula (I), and b) collecting the compound of formula (I) from the extrusion reactor.

19 Claims, No Drawings

CONTINUOUS, SOLVENT-FREE AND NON-ENZYMATIC PEPTIDE SYNTHESIS BY REACTIVE EXTRUSION

FIELD OF THE INVENTION

This invention relates to the field of peptide synthesis

BACKGROUND

Peptides in general are of a high usefulness in various fields of industry, which includes food industry, diagnostic industry, cosmetic industry and therapeutic industry. Therapeutic peptides exhibit a wide array of advantageous characteristics that place them among the most promising active pharmaceutical ingredients (K. Fosgerau, T. Hoffmann, *Drug Discov. Today* 2015, 20, 122; J. L. Lau, M. K. Dunn, *Biorg. Med. Chem.* 2017, DOI: 10.1016/j.bmc.2017.06.052.). Indeed, they are biologically active at very low dose, highly selective, well tolerated and biodegradable into non-toxic amino acids. Yet, industrial production of peptides operates either in solution or by solid phase peptide synthesis (SPPS), and suffers from the huge amounts of toxic organic solvents that are required during the synthesis and purification steps (Bray, *Nature Rev. Drug Discov.* 2003, 2, 587; A. M. Thayer, *Chem. Eng. News* 2011, 89, 21; Mergler et al, *Chimia* 2013, 67, 874; Werbitzky et al., *RSC Drug Discovery Ser.* 2015, 42, 290; Patel, Chem. Eng. News 2017, 95, 27). Although presenting highly concerning environmental issues, polar aprotic solvents such as DMF, DCM, THF and 1,4-dioxane are regularly used (According to Regulation (EC) No 1272/2008, DMF is classified as presenting reproductive toxicity and DCM, THF and 1,4-dioxane as toxic and/or carcinogenic (Category 2). Under the pressure of REACH implementation, pharmaceutical industries have called for alternatives to these solvents (Patel, *Chem. Eng. News* 2017, 95, 27; D. J. C. Constable, P. J. Dunn, J. D. Hayler, G. R. Humphrey, J. J. L. Leazer, R. J. Linderman, K. Lorenz, J. Manley, B. A. Pearlman, A. Wells, A. Zaks, T. Y. Zhang, *Green Chem.* 2007, 9, 411). The development of industrial peptide production is also hampered by the conventional discontinuous batch mode of production as well as by the limitations related to the general low solubility of peptides. In practice, utilisation of a solvent is not mandatory to perform peptide synthesis as long as reactants are ground and mixed together through application of mechanical forces (James et al., *Chem. Soc. Rev.* 2012, 41, 413; Métro, et al., in *Ball Milling Towards Green Synthesis: Applications, Projects, Challenges* (Eds.: A. Stolle, B. Ranu), The Royal Society of Chemistry, 2015, pp. 114). Indeed, the group of Lamaty described in 2009 the solvent-free synthesis of various dipeptides, including the sweetener Aspartame, by grinding together in a ball-mill urethane-protected α-amino acid N-carboxyanhydride (UNCA), α-amino ester salts and NaHCO$_3$(Declerck, et al., *Angew. Chem. Int. Ed.* 2009, 48, 9318). Based on this new paradigm, other developments in the field allowed the production of various peptides, such as the pentapeptide Leu-Enkephalin (Hernández et al., *J. Org. Chem.* 2010, 75, 7107; Štrukil et al., *Chem. Commun.* 2012, 48, 12100; Duangkamol et al., *RSC Adv.* 2015, 5, 52624; Porte et al., *Eur. J. Org. Chem.* 2016, 3505; Landeros et al., *Eur. J. Org. Chem.* 2017, 687; Gonnet et al., *ACS Sustainable Chem. Eng.* 2017, 5, 2936; Hernández et al., *Green Chem.* 2017, 19, 2620; Maurin et al., *Beilstein J. Org. Chem.* 2017, 13, 2087; Pétry et al., *Beilstein J. Org. Chem.* 2017, 13, 2169). Although enabling the production of more than 4 g of a dipeptide for the best case, these approaches were limited to discontinuous batch and lab-scale production, thereby preventing them from a wide dissemination among the peptide industry. More recently, the possibility to synthesize homo-oligo-peptides by enzyme-catalyzed polymerisation of α-L-amino acid ester hydrochlorides by reactive extrusion was described (Ardila-Fierro et al., *Green Chem.* 2018, DOI: 10.1039/C7GC03205F). Yet, such a method does not allow any possibility to finely control the diversity of the α-L-amino acid sequence of the peptide because the polymerisation is based on a single α-L-amino acid ester monomer. In addition, the stereoselectivity of peptide couplings was not demonstrated in the study. Besides, utilisation of this enzyme previously proved inefficient for the coupling of α-D-amino acid residues (Hernández, J. G. et al., *Green Chem.* 2017, 19, 2620-2625). Thus, there is still a need in the art for improved methods of peptide synthesis, including those related to solvent-free peptide synthesis allowing production of higher amounts of peptides than the known solvent-free methods.

SUMMARY

This invention relates to a continuous, solvent-free and non-enzymatic method for synthesizing a compound of formula (I):

$$\text{Ra-POLYPEP-Rc} \tag{I}$$

wherein:

POLYPEP is a poly-amino acid compound,

Ra means a N-protective group;

Rc means-O-Rd, wherein Rd means a hydrogen atom, a (C1-C24 alkyl) group, a methyl group substituted with one or more phenyl groups, a non-substituted (C6-C10) aryl group, a O-protective group or a —NReRf group wherein Re and Rf groups mean, one independently of each other, a hydrogen atom, a (C1-C24) alkyl group, a methyl group substituted with one or more phenyl groups, a non-substituted (C6-C10 aryl) group or a N-protective group, which method comprises the steps of:

a) feeding an extrusion reactor with (1) a compound of formula (II)

$$\text{Ra-PEPNt-Rg} \tag{II}$$

wherein;

PEPNt is a mono- or a poly-amino acid compound,

Ra is as defined for the compound of formula (I), and

Rg is a leaving group and (2) a compound of formula (III)

$$\text{H-PEPCt-Rc} \tag{III}$$

wherein:

PEPCt is a mono- or a poly-amino acid compound, and

Rc is as defined for the compound of formula (I)

in the absence of any solvent, so that the compound of formula (II) and the compound of formula (III) react together for generating a compound of formula (I), and b) collecting the compound of formula (I) from the extrusion reactor.

In some specific embodiments of the disclosed method, compound (II) Ra-PEPNt-Rg consists of a compound of formula (II'):

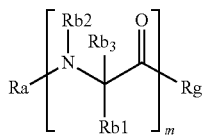

wherein the meaning of each of groups Ra, Rb1, Rb2, Rb3 and Rg are specified further in the present disclosure.

In some specific embodiments of the disclosed method, compound (III) H-PEPCt-Rc consists of a compound of formula (III')

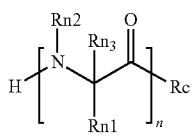

Wherein the meaning of groups Rn1, Rn2, Rn3 and Rc are specified further in the present disclosure.

In some embodiments, each Rb1 group represents, one independently from each other, a hydrogen atom, a (C1-C6) alkyl group non-substituted or substituted by a group selected among an aryl group non-substituted or substituted by an —OH group, —OH, —COOH, —CONH2, —SH, —S—(C1-C6 alkyl), —NH2, —NH—C(NH)(NH2), -imidazolyl and indolyl, In some embodiments, each Rb3 group represents, one independently from each other, a hydrogen atom a (C1-C6) alkyl group non-substituted or substituted by a group selected among an aryl group non-substituted or substituted by an —OH group, —OH, —COOH, —CONH2, —SH, —S—(C1-C6 alkyl), —NH2, —NH—C(NH)(NH2), -imidazolyl and indolyl, In some other embodiments, each paired Rb1 and Rb2, or paired Rb3 and Rb2, one paired Rb1 and Rb2 or one paired Rb2 and Rb3 independently from each other paired Rb1 and Rb2 or paired Rb2 and Rb3, form together with respectively the carbon atom and the nitrogen atom to which they are linked, a heterocyclic ring comprising at least one nitrogen atom.

In some embodiments, each Rn1 represents, one independently from each other, a hydrogen atom, a (C1-C6) alkyl group non-substituted or substituted by a group selected among an aryl group non-substituted or substituted by an —OH group, —OH, —COOH, —CONH2, —SH, —S—(C1-C6 alkyl), —NH2, —NH—C(NH)(NH2), -imidazolyl and indolyl, In some embodiments, each Rn3 represents, one independently from each other, a hydrogen atom, a (C1-C6) alkyl group non-substituted or substituted by a group selected among an aryl group non-substituted or substituted by an —OH group, —OH, —COOH, —CONH2, —SH, —S—(C1-C6 alkyl), —NH2, —NH—C(NH)(NH2), -imidazolyl and indolyl, In some other embodiments, each paired Rn1 and Rn2, or paired Rn3 and Rn2, one paired Rn1 and Rn2 or one paired Rn3 and Rn2 independently from each other paired Rn1 and Rn2 or paired Rn3 and Rn2, form together with respectively the carbon atom and the nitrogen atom to which they are linked, a heterocyclic ring comprising at least one nitrogen atom In some embodiments of the method, step a) comprises adding a base, such as a base selected from the group consisting of a mineral base or an organic base.

In some embodiments of the method, the extrusion reactor is selected among a single screw extrusion reactor and a double screw extrusion reactor.

In some embodiments of the method, step a) is performed by maintaining the reactants at a constant selected temperature, such as at a temperature ranging from 30° C. to 100° C., which includes at a temperature ranging from 35° C. to 70° C.

DETAILED DESCRIPTION

The inventors have conceived a method for peptide synthesis which method allows peptide synthesis in a continuous, solvent-free and non-enzymatic way, thus allowing the production of desired peptides in amounts complying with industrial requirements.

Further, the method conceived by the inventors allows production of the desired peptides with high yields and a high purity, and fully complies with (i) requirements for low environmental impact in view of the low level of liquid additives and non-reacted products and with (ii) economic interest when taken into consideration the high production yield that is reached.

This invention relates to a continuous, solvent-free and non-enzymatic method for synthesizing a compound of formula (I):

Ra-POLYPEP-Rc    (I)

wherein:
POLYPEP is a poly-amino acid compound,
Ra means a N-protective group;
Rc means-O-Rd, wherein Rd means a hydrogen atom, a (C1-C24 alkyl) group, a methyl group substituted with one or more phenyl groups, a non-substituted (C6-C10) aryl group, a O-protective group or a —NReRf group wherein Re and Rf groups mean, one independently of each other, a hydrogen atom, a (C1-C24) alkyl group, a methyl group substituted with one or more phenyl groups, a non-substituted (C6-C10 aryl) group or a N-protective group,
which method comprises the steps of:
a) feeding an extrusion reactor with
(1) a compound of formula (II)

Ra-PEPNt-Rg    (II)

wherein;
PEPNt is a mono- or a poly-amino acid compound,
Ra is as defined for the compound of formula (I), and
Rg is a leaving group
and
(2) a compound of formula (III)

H-PEPCt-Rc    (III)

wherein:
PEPCt is a mono- or a poly-amino acid compound, and
Rc is as defined for the compound of formula (I)
in the absence of any solvent,
so that the compound of formula (II) and the compound of formula (III) react together for generating a compound of formula (I), and b) collecting the compound of formula (I) from the extrusion reactor.

The terms "compound of formula (X)" and "compound (X)", such as "compound of formula (I)" and "compound (I)" may be interchangeably used herein.

The terms "amino acid" and "amino acyl" may be interchangeably used herein. In the conventional use of these terms, "amino acid" encompasses a residue which is not linked to another residue, whereas "amino acyl" encompasses an amino acid residue viewed as a chemical group linked to another chemical group, e.g. another amino acyl residue.

As used herein, in embodiments wherein PEPNt is a mono-amino acid compound, group Ra is linked to the nitrogen atom of the central amino-group of the said amino acid and group Rg is linked to the carbon atom of the central carbonyl group of the said amino acid.

As used herein, in embodiments wherein PEPNt is a poly-amino acid compound, group Ra is linked to the nitrogen atom of the central amino group of the amino acid located at the N-terminal end of the said poly-amino acid compound, and group Rg is linked to the carbon atom of the central acyl group of the amino acid located at the C-terminal end of the said poly-amino acid compound.

As used herein, the "central" amino group of a given amino acid compound consists of the amino group which would be involved in a peptide bond if the said given amino acid compound was bound to another amino acid compound.

As used herein, the "central" carbonyl or acyl group of a given amino acid compound consists of the carbonyl or acyl group which would be involved in a peptide bond if the said given amino acid compound was bound to another amino acid compound.

As used herein, in embodiments wherein PEPCt is a mono-amino acid compound, the hydrogen atom denoted "H" is linked to the nitrogen atom of the central amino-group of the said amino acid and group Rc is linked to the carbon atom of the carbonyl group of the said amino acid.

As used herein, in embodiments wherein PEPCt is a poly-amino acid compound, the hydrogen atom denoted "H" is linked to the nitrogen atom of the central amino group of the amino acid located at the N-terminal end of the said poly-amino acid compound, and group Rc is linked to the carbon atom of the central carbonyl group of the amino acid located at the C-terminal end of the said poly-amino acid compound.

As used herein, POLYPEP is a poly-amino acid compound wherein group Ra is linked to the nitrogen atom of the amino group of the amino acid located at the N-terminal end of the said poly-amino acid compound, and group Rg is linked to the carbon atom of the acyl group of the amino acid located at the C-terminal end of the said poly-amino acid compound.

As used herein, an "amino acid", in its most general definition, consists of a compound comprising a functional primary or secondary amino group and a functional carboxyl group. Illustratively, all natural amino acids comprise a functional primary amino group, except proline which comprises a secondary functional amino group.

By definition, when step a) of the method comprises reacting a compound of formula (II) comprising a number "m" of amino acids with a compound of formula (III) comprising a number "n" of amino acids, the resulting compound of formula (I) comprises a number "m"+"n" of amino acids.

As it will be detailed elsewhere in the present disclosure, there is not a strict limit in the number of amino acids comprised in a compound of formula (II) or in a compound of formula (III), since the same unique reaction step is performed, irrespective of the size of each of compounds (II) and (III).

In some embodiments of the method, PEPNt and PEPCt each exclusively comprises amino acyl residues that are linked through conventional aa1-C(=O)—NH-aa2-amide peptide bonds, wherein aa1 and aa2 each represents an amino acyl residue.

In some other embodiments, one of PEPNt and PEPCt, or both PEPNt and PEPCt, comprises one or more residues that are linked through a non-conventional peptide bond, such as aa1-C(=O)—O-aa2, wherein aa1 represents an amino acyl residue and aa2 represents a non-conventional amino acyl residue wherein the functional amino group is absent. According to these embodiments, at least one conventional amide peptide bond linking to residues is replaced by an ester bond. Peptides wherein two residues are bond by such a non conventional ester bond are well known in in the art and are usually termed "depsipeptides".

In general, compounds (II) and compounds (III) mostly comprise alpha aminoacyl residues, i.e. amino acyl residues wherein the functional amino group is linked to the carbon atom located at the alpha position from the carboxyl group thereof. Illustratively, each of the 20 natural amino acids consists of alpha amino acids.

In some embodiments, one among compound (II) or compound (III), or both compounds (II) and (III), comprise one or more beta amino acyl residues. Beta amino acyl residues, wherein the functional amino group is linked to the carbon atom located at the beta position from the carboxyl group thereof. A well-known beta amino acid is beta alanine.

In some embodiments, one among compound (II) or compound (III), or both compounds (II) and (III), comprise one or more gamma amino acyl residues. Gamma amino acyl residues, wherein the functional amino group is linked to the carbon atom located at the gamma position from the carboxyl group thereof. A well-known gamma amino acid is gamma aminobutyric acid.

In some of the embodiments wherein compound (II), compound (III), or both compounds (II) and (III), consist of a poly-amino acid compound, one among compound (II) or compound (III), or both compounds (II) and (III), comprises a pseudopeptide provided that:
  for compound (II), Ra is linked to the nitrogen atom of the central amino group of the amino acyl residue located at the N-terminal end of compound (II) and that group Rg is linked to the carbon atom of the central carbonyl group of the amino acid located at the C-terminal end of compound (II); and
  for compound (III), the hydrogen atom denoted "H" is linked to the nitrogen atom of the central amino-group of the amino acid located at the N-terminal end group of compound (III) and that Rc is linked to the carbon atom of the central carbonyl group of the amino acid located at the C-terminal end of compound (III).

As used herein, a "pseudopeptide" consists of a compound comprising a chemical chain, most preferably an optionally substituted hydrocarbon chain, which does not exclusively comprise amino acyl residues, wherein the said compound (i) comprises a functional amino group at one end of the said chemical chain, which end may be termed an "N-terminal end" herein, and (ii) comprises a functional carboxyl group at the other end of the chemical chain, which other end may be termed a "C-terminal end" herein.

In some embodiments, compound (II) comprises from 1 to 500 amino acid residues, such as from 1 to 100 amino acid residues, which includes from 1 to 50 amino acid residues.

In some embodiments, compound (III) comprises from 1 to 500 amino acid residues, such as from 1 to 100 amino acid residues, which includes from 1 to 50 amino acid residues.

As already mentioned previously herein, both compounds (II) and (III) may comprise exclusively amino acyl residues that are linked, one with another, through a conventional amide peptide bond.

In some specific embodiments of the disclosed method, compound (II) Ra-PEPNt-Rg consists of a compound of formula (II'):

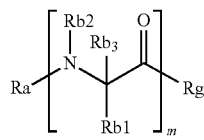

(II')

wherein the meaning of each of groups Ra, Rb1, Rb2, Rb3 and Rg are specified further in the present disclosure.

In some specific embodiments of the disclosed method, compound (III) H-PEPCt-Rc consists of a compound of formula (III')

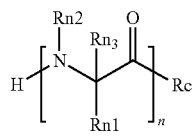

(III')

Wherein the meaning of groups Rn1, Rn2, Rn3 and Rc are specified further in the present disclosure.

These specific embodiments of the disclosed method allow obtaining a compound of formula (I'), as detailed hereunder.

Thus, this invention also relates to a continuous, solvent-free and non-enzymatic method for synthesizing a compound of formula (I')

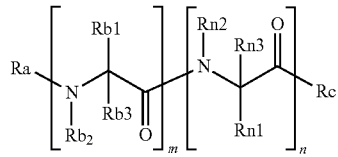

(I')

wherein:
m is an integer of 1 or more,
n is an integer of 1 or more;
Ra means a N-protective group;
each Rb1 represents, one independently from each other, a hydrogen atom, a (C1-C6) alkyl group non-substituted or substituted by a group selected among an aryl group non-substituted or substituted by an —OH group, —OH, —COOH, —CONH2, —SH, —S—(C1-C6 alkyl), —NH2, —NH—C(NH)(NH2), -imidazolyl and indolyl,
Rb2 is selected in the group consisting of a hydrogen atom, an alkyl group, an aryl group or a N-protective group, each Rb3 represents, one independently from each other, a hydrogen atom, a (C1-C6) alkyl group non-substituted or substituted by a group selected among an aryl group non-substituted or substituted by an —OH group, —OH, —COOH, —CONH2, —SH, —S—(C1-C6 alkyl), —NH2, —NH—C(NH)(NH2), -imidazolyl and indolyl, or each paired Rb1 and Rb2, or paired Rb3 and Rb2, one paired Rb1 and Rb2 or one paired Rb2 and Rb3 independently from each other paired Rb1 and Rb2 or paired Rb2 and Rb3, form together with respectively the carbon atom and the nitrogen atom to which they are linked, a heterocyclic ring comprising at least one nitrogen atom and each Rn1 represents, one independently from each other, a hydrogen atom, a (C1-C6) alkyl group non-substituted or substituted by a group selected among an aryl group non-substituted or substituted by an —OH group, —OH, —COOH, —CONH2, —SH, —S—(C1-C6 alkyl), —NH2, —NH—C(NH)(NH2), -imidazolyl and indolyl, Rn2 is selected in the group consisting of a hydrogen atom, an alkyl group or an aryl group, and each Rn3 represents, one independently from each other, a hydrogen atom, a (C1-C6) alkyl group non-substituted or substituted by a group selected among an aryl group non-substituted or substituted by an —OH group, —OH, —COOH, —CONH2, —SH, —S—(C1-C6 alkyl), —NH2, —NH—C(NH)(NH2), -imidazolyl and indolyl, or each paired Rn1 and Rn2, or paired Rn3 and Rn2, one paired Rn1 and Rn2 or one paired Rn3 and Rn2 independently from each other paired Rn1 and Rn2 or paired Rn3 and Rn2, form together with respectively the carbon atom and the nitrogen atom to which they are linked, a heterocyclic ring comprising at least one nitrogen atom Rc means-O-Rd, wherein Rd means a hydrogen atom, a non-substituted (C1-C24 alkyl) group, a methyl group substituted with one or more phenyl groups, a non-substituted (C6-C10) aryl group, or a O-protective group, or a —NReRf group wherein Re and Rf group mean, one independently of each other, a hydrogen atom, a (C1-C24) alkyl group, a methyl group substituted with one or more phenyl groups, a non-substituted (C6-C10 aryl) group or a N-protective group, which method comprises the steps of:
a) feeding an extrusion reactor with
(1) a compound of formula (II')

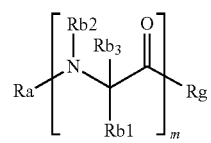

(II')

wherein
m, Ra, Rb1, Rb2 and Rb3 are as defined for the compound of formula (I'), and Rg is a leaving group
and
(2) a compound of the following formula (III')

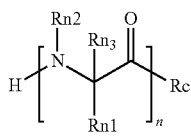

wherein n, Rn1, Rn2, Rn3 and Rc are as defined for the compound of formula (I').

in the absence of any solvent, so that the compound of formula (II') and the compound of formula (III') react together for generating a compound of formula (I'), and b) collecting the compound of formula (I') from the extrusion reactor.

In some embodiments, the compound of formula (I) or the compound of formula (I') encompasses the pharmaceutically acceptable salts thereof.

By the term of "(C1-C24) alkyl group" is meant in the sense of the present invention any linear or branched alkyl group with 1-24 carbon atoms, in particular the methyl, ethyl, n-propyl, isopropyl, n-butyl, iso-butyl, sec-butyl, t-butyl, n-pentyl, n-hexyl groups. Advantageously this is a methyl or t-butyl group.

An "aryl", unless otherwise specified, means an aromatic monocyclic or multicyclic hydrocarbon ring system of 6 to 14 carbon atoms, preferably of 6 to 10 carbon atoms. Exemplary aryl groups include phenyl or naphthyl. Illustratively, a (C6) aryl group is a phenyl.

By the term of "N-protective group" is meant in the sense of the present invention any substituent which protects the NH2 group against undesirable reactions such as the N-protective groups described in Greene, "Protective Groups In Organic Synthesis", (John Wiley & Sons, New York (1981)) and Harrison et al. "Compendium of Synthetic Organic Methods", Vols. 1-8 (J. Wiley & Sons, 1971-1996). The N-protective groups comprise carbamates, amides, N-alkylated derivatives, amino acetal derivatives, N-benzylated derivatives, imine derivatives, enamine derivatives and N-heteroatom derivatives. In particular, the N-protective group comprises the formyl, acetyl, benzoyl, pivaloyl, phenylsulfonyl, benzyl (Bn), t-butyloxycarbonyl (Boc), benzyloxycarbonyl (Cbz), p-methoxybenzyloxycarbonyl, p-nitrobenzyl-oxycarbonyl, trichloroethoxycarbonyl (Troc), allyloxycarbonyl (Alloc), 9-fluorenylmethyloxycarbonyl (Fmoc), trifluoroacetyl group, benzyl carbamates (either substituted or not) and the like. Either Boc or Cbz as a N-protective group is advantageous to use because of the relative facility of removal, for example with moderate acids in the case of Boc, for example trifluoroacetic acid, or hydrochloric acid in ethyl acetate; or by catalytic hydrogenation in the case of Cbz. Advantageously, this is the Boc group.

By the term of "O-protective group" is meant in the sense of the present invention any substituent which protects the hydroxyl or carboxyl group, i.e. a reactive oxygen atom, against undesirable reactions, such as the O-protective groups described in Greene, "Protective Groups In Organic Synthesis", (John Wiley & Sons, New York (1981)) and Harrison et al. "Compendium of Synthetic Organic Methods", Vols. 1-8 (J. Wiley & Sons, 1971-1996). The O-protective groups comprise methyl or alkyl ethers either substituted or not, for example methoxymethyl, benzyloxymethyl, 2-methoxyethoxymethyl, 2-(trimethylsilyl)ethoxymethyl, t-butyl, benzyl and triphenylmethyl, benzyl ethers (either substituted or not), tetrahydropyranyl ethers, allyl ethers, substituted ethyl, for example 2,2,2-trichloroethyl, ethers, silyl ethers or alkylsilyl ethers, for example trimethylsilyl, t-butyl dimethyl silyl, and t-butyldiphenyl silyl, heterocyclic ethers; and esters prepared by reaction of the hydroxyl group with a carboxylic acid, for example tert-butyl, benzyl, or methyl esters, carbonates in particular benzyl carbonate or haloalkyl carbonate, acetate, propionate, benzoate and the like. Advantageously this is the benzyl group.

Subsequently, the compounds of formula (I') may be deprotected so as to obtain the peptides for which the —OH, —NH2, —SH, —NH, —CONH2 and —COOH functions are non-protected.

By the term "leaving group" is meant in the sense of the invention any chemical group that allows the group —C(O)-Rg of the compound of formula (II') to react with the group NH—Rn2 of the compound of formula (III'). Thus, leaving groups encompass any of those which are well known from the one skilled in the art, and which are used in coupling reaction between two amino acid residues in known chemical of peptide synthesis. Leaving groups may for example be selected in the group consisting of N-substituted carbamates, pentafluorophenyl hydroxylate and succinimidyl N-hydroxylate. Leaving groups encompass those selected in the group consisting of imidazolate, benzimidazo late, benzotriazole N-hydroxylate, azabenzotriazole N-hydroxylate, pyrimidine hydroxylate, triazine hydroxylate, paranitrophenyl hydroxylate and oximate (such as Oxyma®). Leaving groups also encompass those selected in the group of halides such as fluorides, bromides and chlorides. Leaving groups also encompass those selected in the group of carboxylates and carbonates. Leaving groups encompassed therein may be found by the one skilled in the art in the publication of El-Faham et al. (2011, Chemical reviews, Vol. 111(11): 6557-6602).

By "paired" groups, Rb1 and Rb2, Rb3 and Rb2, Rn1 and Rn2, or Rn3 and Rn2, it is intended herein that the paired two groups are part of the same monomer unit of a compound (I'), (II') or (III'), and wherein the first group of a paired group (among the first groups Rb1, Rb3, Rn1, Rn3) is linked to a carbon atom which is adjacent to the nitrogen atom to which is linked the second group of the paired groups.

A compound of formula (I') is thus formed of m units comprising groups Rb1, Rb2 and Rb3 and of n units comprising groups Rn1, Rn2 and Rn3. Each unit comprising groups Rb1, Rb2 and Rb3 may be termed an amino acid residue herein, although the more precise term aminoacyl group may also be used. Each unit comprising groups Rn1, Rn2 and Rn3 may be termed an amino acid residue herein, although the more precise term aminoacyl group may also be used.

Then, a compound of formula (I'), which comprises a number of "m+n" amino acid residues, may be termed a peptide herein.

As it will be described in more detail elsewhere in the present specification, some combinations of meanings of Rb1, Rb2 and Rb3 define a unit consisting of a natural amino acid, i.e. a natural aminoacyl group. Also, some combinations of meanings of Rn1, Rn2 and Rn3 define a unit consisting of a natural amino acid, i.e. a natural aminoacyl group.

The continuous peptide synthesis method described herein consists of a method of solvent-free and non-enzymatic synthesis by reactive extrusion.

As it will be described in the present application, the continuous peptide synthesis method herein is a non-enzymatic method of peptide synthesis, which means that the said method is performed in the absence of any added enzyme. The method herein is a purely chemical method for solvent-free peptide synthesis.

A compound of formula (I') comprises m+n monomer units forming a polymer chain of these m+n units.

As used herein, a compound of formula (I') may be termed a peptide, i.e. a peptide of formula (I'), wherein the m number of monomer units brought by compound (II') are located at the "N-terminal" end thereof and wherein the n number of monomer units brought by compound (III') are located at the "C-terminal" end thereof, by reference to the nomenclature that is conventionally used as regards conventional, e.g. natural, peptides.

Further, the continuous peptide synthesis method described herein allows obtaining compounds of formula (I') comprising distinct monomer units, since (i) groups Rb1, Rb2 and Rb3 of a first given monomer unit may be distinct from (ii) groups Rb1, Rb2 and Rb3 of a second given monomer unit. Similarly, (i) groups Rn1, Rn2 and Rn3 of a first given monomer unit may be distinct from (ii) groups Rn1, Rn2 and Rn3 of a second given monomer unit. Yet similarly, (i) groups Rb1, Rb2 and Rb3 of a first given monomer unit may be distinct from (ii) groups Rn1, Rn2 and Rn3 of a second given monomer unit.

Otherwise said, according to the continuous peptide synthesis method described herein, a compound of formula (I), which includes a compound of formula (I'), is not limited to an homopolymer of m+n monomer units, and thus encompasses an heteropolymer of m+n monomer units, wherein at least two of the said monomer units comprised therein are distinct, one from the other.

Thus, in some embodiments wherein the units comprised in a compound of formula (I), which includes a compound of formula (I'), consist of natural amino acid residues, the continuous method of synthesis described herein allows obtaining peptides of a determined amino acid sequence, such as a peptide of a therapeutic usefulness.

Further, in some specific embodiments of a compound (I) which encompasses a compound (I'), it is expressly excluded that all monomer units comprised therein are identical. Otherwise said, according to these specific embodiments of a compound (I) or (I'), the said compound (I) or (I') does not consists of a homopolymer compound, such as does not consist of a homopolymer of a given amino acid residue, e.g. a poly-Ala peptide.

As it directly flows from the content of the present disclosure, the continuous method of peptide synthesis herein allows a complete control of the sequence of the units chain comprised in a compound (I) or (I'). Otherwise said, in illustrative embodiments wherein the monomer units consist of natural amino acids, the continuous method of peptide synthesis herein allows a complete control of the amino acid sequence of the resulting peptide of formula (I) or (I').

Unexpectedly, the inventors have shown that compounds of formula (I) or (I') may be synthesized in the absence of any solvent by bringing into contact (i) an activated first amino acid or an activated first peptide of formula (II) or (II') and (ii) a reactive second amino acid or a reactive second peptide of formula (III) or (III'), inside an extrusion reactor.

Unexpectedly, the inventors have also shown that compounds of formula (I) or (I') may be synthesized in the absence of any solvent by bringing into contact (i) an activated first amino acid or an activated first peptide of formula (II) or (II') and (ii) a reactive second amino acid or a reactive second peptide of formula (III) or (III') and (iii) a base, inside an extrusion reactor.

In some preferred embodiments, (i) the said first amino acid or first peptide of formula (II) or (II') to be added and (ii) the said second amino acid or the said second peptide of formula (III) or (III'), which react together to form a compound of formula (I) or (I'), are both provided in a solid form, generally under a solid state, preferably under the form of a powder. According to these preferred embodiments of the method, step a) also comprises adding a liquid additive so as to reduce the viscosity of the mixture of compounds (II) or (II') and (III) or (III') and so as to improve the mixing of compounds (II) or (II') and (III) or (III').

In some other preferred embodiments, one of the compounds (II) (or (II')) or (III) (or (III')) is in a liquid form. Illustratively, one of the compounds (II) (or (II')) or (III) (or (III')) consists of a solution of the said compound. According to these other embodiments, performing step a) of the continuous synthesis method does not require addition of a liquid additive since the appropriate viscosity of the reaction mixture is already reached by the liquid additive contained in the solution of compound (II) (or (II')) or (III) (or (III')).

The successful and complete reaction between these two main reactants is all the more surprising that the shear forces that are generated into an extrusion reactor simply allow an homogeneous mixing of these two main reactants, without a substantial powder particle size reduction and thus without substantially increase of the active surface, in contrast to the grinding forces exerted in other kind of reactors such as a ball-mill device. Also, the successful and complete reaction between the two compounds (II) or (II') and (III) or (III') is all the more surprising because it is known than the mechanical forces applied to a reaction mixture in an extruder are of completely distinct nature and of much lower intensity when compared to the forces applied in other types of reactors, and especially to those applied in a ball-mill device.

In some preferred embodiments of the continuous synthesis method herein, step a) is performed in the absence of an added base, as shown in some examples.

In some preferred embodiments of the continuous synthesis method herein, step a) comprises adding a base, as shown in other examples.

In some other preferred embodiments of the method, especially those where compound (III) or (III') is under the form of a salt, the said salt may be selected in the group comprising hydrochloride, hydrobromide, acetate, trifluoroacetate, fumarate, alkylsulfonate, arylsulfonate or dibenzenesulfonamidate salt.

The successful and complete reaction which is obtained with the continuous method herein means that, unexpectedly, the use of an extrusion reactor device allows a simultaneous contact of the three reagents required for the reaction completion, namely (1) the compound of formula (II) or (II') and (2) the compound of formula (III) or (III'), or alternatively (1) the compound of formula (II) or (II') and (2) the compound of formula (III) or (III') and (3) the base. Thus, unexpectedly, the continuous method herein allows a high yield peptide synthesis when adding simultaneously, or almost simultaneously, the three required reagents for forming the initial reaction mixture.

Although reactive extrusion has been widely used in the food and plastic industry, and also identified as interesting in the pharmaceutical industry, production of high added-value chemicals by reactive extrusion has been scarce (Jiménez-González et al., *Org. Process Res. Dev.* 2011, 15, 900; Dhumal et al., *Pharm. Res.* 2010, 27, 2725; Medina et al., *J. Pharm. Sci.* 2010, 99, 1693; Daurio et al., *Faraday Discuss.* 2014, 170, 235; Crawford et al., *Chem. Sci.* 2015, 6, 1645; Crawford et al., *Chem. Commun.* 2016, 52, 4215; Karak et al., *J. Am. Chem. Soc.* 2017, 139, 1856; Crawford et al., *Green Chem.* 2017, 19, 1507; Crawford et al., *Chem. Commun.* 2017, 53, 13067; Isoni et al., *Org. Process Res. Dev.* 2017, 21, 992; Ardila-Fierro et al., *Green Chem.* 2018, DOI: 10.1039/C7GC03205F). First examples reported in the literature described the formation of organic co-crystals. Later on, reactive extrusion was applied to the synthesis of metal-organic-frameworks (MOF), deep eutectic solvents (DES), covalent-organic-frameworks (COF), and α,β-unsaturated carbonyls and imines by condensation reactions. Reduction of aldehydes with $NaBH_4$ by reactive extrusion has also been described. More recently, the possibility to synthesize homo-oligo-peptides by enzyme-catalyzed polymerisation of α-L-amino acid esters hydrochlorides by reactive extrusion was described (Ardila-Fierro et al., *Green Chem.* 2018, DOI: 10.1039/C7GC03205F). Yet, such a method does not allow any possibility to finely control the diversity of the α-L-amino acid sequence of the peptide because the polymerisation is based on a single α-L-amino acid ester monomer. In addition, the stereoselectivity of the peptide couplings was not demonstrated in the study. Besides, utilisation of this enzyme previously proved inefficient for the coupling of α-D-amino acid residues (Hernández, J. G. et al., *Green Chem.* 2017, 19, 2620-2625). It is well-known for the one skilled in the art that enzyme-catalyzed peptide couplings are inefficient for coupling α-D-amino acid residues, while chemical methods are equally efficient for coupling both L and D amino acid residues.

According to the inventors' knowledge, it is described herein for the first time a non-enzymatic method for peptide synthesis which makes use of an extrusion reactor. This method enables to finely control the diversity of the α-amino acid sequence of the peptide, the synthesis of which is sought.

The continuous and solvent-free peptide synthesis method described herein allows a complete conversion of the reactants into the desired peptide.

As it is shown in the examples, the continuous synthesis method described herein overcomes the major hurdles of industrial peptide production.

Extruders are composed of a barrel containing one or two rotating screws enabling the efficient transport and mixing of materials through compression and shearing forces. Of note, the presence of a recirculation pipe can allow, in some embodiments of the continuous synthetic method, to control the residence time of the material to be extruded. Advantageously, this type of equipment allows to work under controlled and continuous flow conditions, while the barrel can be heated up to induce a melted phase facilitating the overall extrusion of the reaction mixture.

On the contrary to classical solution-based flow chemistry that is not compatible with viscous liquids and/or insoluble solids, extruders enable the efficient mixing of viscous and/or solid-containing reaction mixtures.

As it is shown in the examples, the continuous synthesis method described herein allows production of peptides wherein the amino acid units have maintained their initial enantiomeric form. Otherwise said, it is shown in the examples, the continuous synthesis method described herein allows controlling the addition of the L-enantiomer or the D-enantiomer of a given amino acid to a second amino acid or to a peptide chain by reacting the desired amino acid enantiomer at step a) of the method.

The continuous synthesis method herein may be performed in a variety of extrusion reactor devices known in the art.

In some embodiments, the continuous synthesis method herein is performed in a single screw reactor device.

In preferred embodiments, the continuous synthesis method herein is performed in a double screw reactor device, which may also be termed a twin-screw reactor device.

Without wishing to be bound by any particular theory, the inventors believe that performing the continuous synthesis method herein with a double screw reactor device allows a better intimate mixing of the reactants, the compound of formula (II) or (II'), the compound of formula (III) or (III') and optionally the base, respectively.

In some preferred embodiments, step a) is performed by maintaining the reactants at a constant selected temperature. As used herein, a "constant" temperature means a temperature (i) which is substantially the same in the whole mass of the reaction mixture when considering a particular cross section of the extruder barrel and (ii) which is substantially the same at different locations of the reaction mixture along the length of the extruder barrel. As used herein, a constant temperature encompasses a temperature value which varies of +/−10% as compared with the desired temperature set-point value.

In some other preferred embodiments of the continuous method herein, step a) is performed by varying the temperature during the reaction between compounds (II) or (II') and (III) or (III'). Illustratively, after addition of compounds (II) or (II') and (III) or (III') and optionally a base at the beginning of step a), at the feeding end of the extruder which is programmed for maintaining the initial reaction mixture at a first selected temperature A, the temperature of the reaction mixture may be varied with the progression of the said reaction mixture along the barrel of the extruder device, e.g. the temperature of the reaction mixture may be increased with the progression of the said reaction mixture along the barrel of the extruder device. Illustratively, the extruder barrel temperature may be programmed so as to apply a temperature profile of the reaction mixture with its progression along the extruder barrel, i.e. to apply a temperature profile of the reaction mixture with the progression of the reaction completion. Applying a selected temperature profile for performing the reaction between compounds (II) or (II') and (III) or (III'), and optionally a base, allows a more precise control of the reaction step a) and may further increase the yield of the said reaction whereas decreasing or completely avoiding hydrolysis of one or both of the reactants. Applying a temperature profile at step a) of the continuous method may be easily performed by the one skilled in the art, illustratively by using an extruder device equipped with a plurality of heating means located along the extruder barrel and wherein the temperature of each of these heating means may be separately controlled.

Thus, in some embodiments of the continuous synthesis method herein, it may be applied a temperature profile to step a) according to which, for instance, the reaction mixture of compounds (II) or (II') and (III) or (III') and optionally a base is put at a starting temperature $T1°$ C. when introduced at the feeding end of the extruder barrel, and then the temperature of the reaction mixture is progressively increased until a reaction temperature $T2°$ C., e.g. through a programmed temperature ramping slope, before a subsequent decrease of the temperature of the reaction mixture towards a temperature T3° C. which may represent the temperature at which the reaction mixture, or more precisely the material comprising the synthesized compound (I), is collected from the extrusion device, at step b) of the method.

These preferred embodiments are rendered available by the possibility to finely control the temperature of the reaction mixture in an extrusion reactor device.

Generally, extrusion reactor devices are equipped with cast metal split cylinders, such as cast steel split cylinders, with insulated resistance wires embedded therein. An illustrative heater device is a mica band heaters comprising coated resistance wires sandwiched between mica insulation with a steel enclosure for support. In some embodiments of an extrusion reactor device, the heater device may also consist of a known ceramic heater. Irrespective of the kind of heater device which is used, these are in closed contact with the extruder barrel so as to allow a high energy transfer capacity and a control of a homogeneous temperature of the reaction mixture throughout both across and along the extruder barrel.

Such a fine temperature control, notably such a control of a homogeneous temperature control throughout whole of the mass of the reaction mixture, when performing the continuous synthesis method herein, allows performing the said continuous method in a highly reproducible manner, including ensuring reproducibility of the continuous synthesis method as regards to the yield of the resulting peptide production, of the enantiomeric purity of the thus synthesized peptide, as well as of the low level of hydrolysis of the reactants, illustratively of the reduced or even undetectable hydrolysis of the compound of formula (II) or (II').

Such a fine and constant temperature control of the reaction mixture cannot be performed with other kinds of reactors, typically with ball-milling reactors.

As it is shown in the examples, the one skilled in the art may adapt the reaction temperature, optionally the reaction temperature profile, according to the kind of reaction conditions that are desired. The experimental data contained in the examples give a full guidance to the one skilled in the art on optimal temperature conditions for performing the continuous synthesis method herein, notably according to the reaction time period which is sought.

However, in preferred embodiments, the said one skilled in art will use temperature conditions that allow minimizing hydrolysis of the reactants, illustratively minimizing hydrolysis of the compound of formula (II).

In some embodiments, step a) is performed at a temperature ranging from 30° C. to 100° C.

In some embodiments, step a) is performed at a temperature ranging from 35° C. to 70° C.

In some embodiments, step a) is performed at a temperature ranging from 55° C. to 100° C., such as ranging from 55° C. to 90° C.

The examples herein allow the one skilled in the art to select the appropriate reaction conditions, which depend (i) on the temperature of the reaction mixture and (ii) on the duration of step a). As shown in the examples herein, increasing the temperature of the reaction mixture allows reducing the reaction time, i.e. the duration of step a), to obtain the resulting compound of formula (I) or (I').

Other general conditions of step a) of the continuous synthesis method may be easily determined by the one skilled in the art, notably, such as the length of the extruder barrel, the number of screws, the screw profile(s) as well as the rotating speed of the extruder screw(s).

In some embodiments, the duration of step a) of the method ranges from 30 seconds to 120 minutes, advantageously from 1 minute to 20 minutes.

As it is shown in the examples, increasing the rotating speed value of the extruder screw(s) may increase the reaction yield for a given reaction period of time. Illustrative screw rotating speed values are disclosed in the examples herein.

Illustratively, the screw rotating speed value may range from 30 rpm (rounds per minute) to 200 rpm, such as from 50 rpm to 150 rpm, depending notably of the temperature conditions for step a).

Optimal reaction conditions of step a) of the continuous synthesis method may be easily determined by the one skilled in the art in the light of the examples herein and of his general technical knowledge, e.g. selecting an extrusion reactor device wherein the barrel length and the screw profile are adapted for reaction, taken into account the speed of progression of the reaction mixture along the length of the extrusion barrel, the desired peptide is effectively obtained when performing step b) of collecting the compound of formula (I) at the exit of the extrusion barrel.

In some embodiments of the method, it may be used an extrusion reactor equipped with a barrel, the length or screw profile of which does not allow a sufficient residence time of the reaction mixture for the reaction to completely occur at the end of it. In these embodiments, it is preferred to make use of an extrusion barrel comprising a recirculation pipe, so that the reaction will be completed during a further passage of the reaction mixture within the extrusion barrel. According to these embodiments it is performed a recirculation of the reaction mixture until the reaction between the compounds of formula (II) or (II') and of formula (III) or (III') is complete for generating the compound of formula (I). According to some of these specific embodiments, the reaction mixture may be recirculated toward the feeding end of the extruder barrel, while fresh reactants, i.e. compound (II) or (II'), compound (III) or (III') and optionally a liquid additive and/or a base, go on being added into the extruder barrel.

In preferred embodiments, it is made use of an extrusion barrel of a length and screw profile that are sufficient to complete the reaction between the compounds of formula (II) or (II') and of formula (III) or (III') for generating the compound of formula (I) or (I') after a single passage of the reaction mixture through the extrusion barrel.

In some embodiments of the continuous synthesis method described herein, step a) may be performed at a temperature ranging from 30° C. to 100° C., such as ranging from 55° C. to 100° C., during a period of time ranging from 30 seconds to 20 minutes, using a twin-screw extruder device and by applying a rotating speed ranging from 30 rpm (rounds per minute) to 200 rpm, which encompasses a rotating speed ranging from 50 rpm to 150 rpm.

In some embodiments of the continuous synthesis method described herein, when groups Rb1 and Rb2 of a compound (II') form together with respectively the carbon atom and the nitrogen atom to which they are linked, a heterocyclic ring comprising at least one nitrogen atom, the said heterocyclic ring is a pyrrolidinyl group. This encompasses embodiments of the continuous synthesis method wherein the compound of formula (II') comprises a prolyl residue. In certain of these embodiments wherein the said Rb1 and Rb2 group belong to the unit to which is directly linked the Rg group, it encompasses embodiments of the continuous peptide synthesis method wherein the compound (II') comprises an activated prolyl end residue, such as an activated prolyl C-terminal residue.

In some embodiments of the continuous synthesis method described herein, when groups Rb3 and Rb2 of a compound (II') form together with respectively the carbon atom and the nitrogen atom to which they are linked, a heterocyclic ring comprising at least one nitrogen atom, the said heterocyclic ring is a pyrrolidinyl group. This encompasses embodiments of the continuous synthesis method wherein the compound of formula (II') comprises a prolyl residue. In certain of these embodiments wherein the said Rb3 and Rb2 group belong to the unit to which is directly linked the Rg group, it encompasses embodiments of the continuous peptide synthesis method wherein the compound (II') comprises an activated prolyl end residue, such as an activated prolyl C-terminal residue.

In some embodiments of the continuous synthesis method described herein, when groups Rn1 and Rn2 of a compound (III') form together with respectively the carbon atom and the nitrogen atom to which they are linked, a heterocyclic ring comprising at least one nitrogen atom, the said heterocyclic ring is a pyrrolidinyl group. This encompasses embodiments of the continuous synthesis method wherein the compound of formula (III') comprises a prolyl residue.

In some embodiments of the continuous synthesis method described herein, when groups Rn3 and Rn2 of a compound (III') form together with respectively the carbon atom and the nitrogen atom to which they are linked, a heterocyclic ring comprising at least one nitrogen atom, the said heterocyclic ring is a pyrrolidinyl group. This encompasses embodiments of the continuous synthesis method wherein the compound of formula (III') comprises a prolyl residue.

In some embodiments of the continuous synthesis method described herein, in a monomer unit contained in a compound (I') or (II'), thus for a paired Rb1 and Rb3 groups, one of groups Rb1 or Rb3 represents a hydrogen atom a (C1-C6) alkyl group non-substituted or substituted by a group selected among an aryl group non-substituted or substituted by an —OH group, —OH, —COOH, —CONH2, —SH, —S—(C1-C6 alkyl), —NH2, —NH—C(NH)(NH2), -imidazolyl and indolyl, and the other group among groups Rb1 and Rb3 is a hydrogen atom. In some of these embodiments, Rb2 is a hydrogen atom.

In some embodiments of the continuous synthesis method described herein, in a monomer unit contained in a compound (I') or (II'), Rb1 or Rb3 is selected in a group consisting of hydrogen atom, a methyl group, —CH2-CH2-CH2-NH—C(=NH)NH2, —CH2-C(=O)—NH2, —CH2-COOH, —CH2-SH, —(CH2)2-C(=O)—NH2, —(CH2)2-COOH—CH2-Imidazolyl, —CH(CH3)-CH2-CH3, —CH2-CH(CH3)2, —(CH2)4-NH2, —CH2-CH2-S—CH3, —CH2-Phenyl, —CH2OH, —CH(OH)—CH3, —CH2-indolyl, —CH2-phenyl-OH and isopropyl group, and the other among Rb1 and Rb3 is a hydrogen atom. In some of these embodiments, Rb2 is a hydrogen atom. This encompasses embodiments wherein the compound of formula (II') comprises one or more amino acid residues selected in the group consisting of Glycine residue, Alanine residue, Arginine residue, Asparagine residue, Aspartic acid residue, Cysteine residue, Glutamine residue, Glutamic acid residue, Histidine residue, Isoleucine residue, Leucine residue, Lysine residue, Methionine residue, Phenylalanine residue, Serine residue, Threonine residue, Tryptophane residue, Tyrosine residue and Valine residue.

In some embodiments of the continuous synthesis method described herein, in a monomer unit contained in a compound (I') or (III'), thus for a paired Rn1 and Rn3 groups, one of groups Rn1 or Rn3 represents a hydrogen atom, a (C1-C6) alkyl group non-substituted or substituted by a group selected among an aryl group non-substituted or substituted by an —OH group, —OH, —COOH, —CONH2, —SH, —S—(C1-C6 alkyl), —NH2, —NH—C(NH)(NH2), -imidazolyl and indolyl, and the other group among groups Rn1 and Rn3 is a hydrogen atom. In some of these embodiments, Rn2 is a hydrogen atom.

In some embodiments of the continuous synthesis method herein, in a monomer unit contained in a compound (I') or (III'), Rn1 or Rn 3 is selected in a group consisting of hydrogen atom, a methyl group, —CH2-CH2-CH2-NH—C(=NH)NH2, —CH2-C(=O)—NH2, —CH2-COOH, —CH2-SH, —(CH2)2-C(=O)—NH2, —(CH2)2-COOH, —CH2-Imidazolyl, —CH(CH3)-CH2-CH3, —CH2-CH(CH3)2, —(CH2)4-NH2, —CH2-CH2-S—CH3, —CH2-Phenyl, —CH2OH, —CH(OH)—CH3, —CH2-indolyl, —CH2-phenyl-OH, an isopropyl group and Rn2 is a hydrogen atom. In some of these embodiments, Rn2 is a hydrogen atom. This encompasses embodiments wherein the compound of formula (III) comprises one or more amino acid residues selected in the group consisting of Glycine residue, Alanine residue, Arginine residue, Asparagine residue, Aspartic acid residue, Cysteine residue, Glutamine residue, Glutamic acid residue, Histidine residue, Isoleucine residue, Leucine residue, Lysine residue, Methionine residue, Phenylalanine residue, Serine residue, Threonine residue, Tryptophane residue, Tyrosine residue and Valine residue.

In some preferred embodiments of the continuous synthesis method described herein, step a) does not comprise addition of a base.

In some other preferred embodiments of the continuous synthesis method described herein, step a) comprises the addition of a base. In these preferred embodiments, the base which is used at step a) may be selected in the group consisting of any known mineral base such as carbonates and phosphates. In some other of these preferred embodiments, the base may be a hydroxide, such as a hydroxide selected in the group comprising sodium hydroxide, lithium hydroxide, cesium hydroxide, as well as barium or calcium hydroxide. In some further of these preferred embodiments, the base may be an organic base, such as a base selected in the group comprising triethylamine, N,N-diisopropylethylamine and 1,8-diazabicyclo[5.4.0]undec-7-ene (DBU), sodium or potassium methoxide, tetrabutylammonium hydroxide, pyridine, sodium or potassium bis(trimethylsilyl)amide.

Thus, in some preferred embodiments of the continuous synthesis method herein, step a) comprises adding a base.

In some other preferred embodiments of the method, especially those where compound (III) or (III') is under the form of a salt, the said salt may be selected in the group comprising hydrochloride, hydrobromide, acetate, trifluoroacetate, fumarate, alkylsulfonate, arylsulfonate or dibenzenesulfonamidate salt.

In these embodiments, the added base reacts with the compound (III) or (III') so as to generate a deprotonated compound (III) or (III') which becomes highly reactive for reacting with a compound (II) or (II').

In the embodiments wherein the base which is used at step a) of the continuous synthesis method is selected among carbonates, the said carbonate is preferably selected in the group consisting of sodium hydrogenocarbonate, potassium hydrogenocarbonate, cesium hydrogenocarbonate, sodium carbonate, potassium carbonate and cesium carbonate.

The amount of base to be added in these embodiments of step a) of the continuous method of synthesis herein, irrespective of the kind of base which is added, may be easily determined by the one skilled in the art. The one skilled in the art may easily determine the amount of base that will allow a deprotonation of a compound (III) or (III').

Illustratively, the one skilled in the art may refer to pKa of the compound of formula (III) or (III') to determine the type of base used at step a) that will cause the compound of formula (III) or (III') to be deprotonated. Illustratively, in the embodiments wherein the unit comprising group Rc consists of a hydrochloride salt of a natural amino acid methyl ester, the base $NaHCO_3$ is basic enough to deprotonate the hydrochloride salt of the natural amino acid methyl ester thus enabling the free base of the natural amino acid methyl ester to react with compound of formula (II) or (II').

In some embodiments, the selected base which may be added at the beginning of step a) is under a solid state, preferably under the form of a powder.

In some other embodiments, the selected base which may be added at the beginning of step a) is in a liquid form, e.g. a liquid base solution. As is it is shown in the examples, the reaction between a compound of formula (II) or (II') and a compound of formula (III) or (III') is stoichiometric.

Thus, in preferred embodiments of the continuous synthesis method described herein, substantially equimolar amounts of each of compounds of formula (II) or (II') and (III) or (III') are provided to feed the extrusion reactor at the beginning of step a).

As used herein, "substantially equimolar amounts" of two compounds, e.g. of the compounds of formula (II) or (II') and (III) or (III'), means that the number of moles of the most abundant compound is in excess by at most 15% the number of moles of the other compound.

In preferred embodiments of step a) of the continuous synthesis method described herein, the compound of formula (II) or (II') is provided in 10% molar excess as compared with the compound of formula (III) or (III').

In further preferred embodiments, wherein a base is added at step a) of the method, the base is added at step a) also in a "substantially equimolar amounts" as compared to the respective molar amounts of the most abundant among the compounds of formula (II) or (II') and (III) or (III').

According to these further preferred embodiments, the base may be added in a molar excess as compared with both the compound of formula (II) or (II') and the compound of formula (III) or (III').

Illustratively, in some embodiments of the continuous synthesis method described herein, the reactants may be added at step a) in the respective molar amounts of (i) 1 molar equivalent of compound (II) or (II'), (ii) 1.1 molar equivalent of compound (III) or (III') and 1.2 molar equivalent of the base, e.g. a carbonate such as sodium hydrogen carbonate.

In some embodiments of a compound of formula (I) or (I'), or of a compound of formula (II) or (II'), Ra is selected, one independently of each other, in the group consisting of tert-butyloxycarbonyl, 9-fluorenylmethyloxycarbonyl, benzyloxycarbonyl and nitro-veratryloxycarbonyl.

In some embodiments of a compound of formula (I) or (I'), or of a compound of formula (III) or (III'), group Rc means —O-Rd wherein Rd is a benzyl group.

In some embodiments of a compound of formula (I) or of a compound of formula (III) or (III'), Re and Rf are selected, one independently of each other, in the group consisting of a hydrogen atom, a (C1-C24) alkyl group, a methyl group substituted with one or more phenyl groups, a non-substituted (C6-C10) aryl group or a N-protective group such as tert-butyloxycarbonyl, 9-fluorenylmethyloxycarbonyl, benzyloxycarbonyl and nitro-veratryloxycarbonyl.

In some embodiments of a compound of formula (I) or (I') or of a compound of formula (III) or (III'), one of groups Re and Rf, or both groups Re and Rf, represent a benzyl group.

In some embodiments of a compound of formula (I) or (I'), or of a compound of formula (II) or (II'), Ra is a tert-butyloxycarbonyl.

The leaving group Rg may be selected in the group consisting of N-substituted carbamates, pentafluorophenyl hydroxylate, succinimidyl N-hydroxylate, imidazolate, benzimidazolate, benzotriazole N-hydroxylate, azabenzotriazole N-hydroxylate, pyrimidine hydroxylate, triazine hydroxylate, paranitrophenyl hydroxylate, oximate (such as Oxyma®), fluoride, bromide, chloride, carboxylates and carbonates.

In some embodiments, the activated group Rg consists of a hydroxysuccinimidyl group (also termed "OSu" herein).

In some embodiments, the radicals NH2, NH, COOH, CONH2, OH, SH of the Rb1 group and of the Rb3 group of the compound of formula (I') or (II') and of the Rn1 and Rn3 groups of the compounds of formula (I') or (III') are protected by one or more identical or different N-protective or O-protective or S-protective groups. In some of these embodiments, the N-protective groups are identical to group Ra, in which case the whole N-protective groups may be simultaneously removed when desired. In some other embodiments, one or more of the N-protective groups is distinct or not from group Ra, in which case Ra and one or more of the other N-protective groups may be selectively removed.

In some preferred embodiments, the compound of formula (III) or (III') is provided at step a) under the form of a salt. Salts of a compound of formula (III) or (III') may be selected in the group consisting of sodium salt, potassium salt, lithium salt, hydrochloride, hydrobromide, acetate, trifluoroacetate, fumarate, alkylsulfonate, arylsulfonate and dibenzenesulfonamidate. An illustration is disclosed in the examples which is the sodium glycinate.

There is not a strict limit in the number of monomer units, e.g. in the number of amino acid residues, that may be comprised in a compound of formula (I) or (I'). The examples herein illustrate performing the continuous synthesis method for generating compounds of formula (I) or (I') which consist of dipeptides and tripeptides. It is pointed out that the reaction yield does not detectably decrease with the length of the compound of formula (I) or (I') which is produced.

For the compounds of formula (I) or (I') and of formula (II) or (II'), m is an integer of 1 or more, which encompasses n values ranging from 1 to 500, n values ranging from 1 to 200, n values ranging from 1 to 100, n values ranging from 1 to 50, n values ranging from 1 to 40, n values ranging from 1 to 30, n values ranging from 1 to 20 and n values ranging from 1 to 10.

For the compounds of formula (I) or (I') and of formula (III) or (III'), n is an integer of 1 or more, which encompasses n values ranging from 1 to 500, n values ranging from 1 to 200, n values ranging from 1 to 100, n values ranging from 1 to 50, n values ranging from 1 to 40, n values ranging from 1 to 30, n values ranging from 1 to 20 and n values ranging from 1 to 10.

In some embodiments, m is an integer having a value selected in the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100.

In some embodiments, n is an integer having a value selected in the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100.

The examples illustrate embodiments of the continuous synthesis method wherein m is 1 and n is 1 or 2.

In some embodiments of the continuous synthesis method described herein, and especially in the embodiments thereof wherein the compound (II) or (II'), the compound (III) or (III'), and optionally a base, are added at step a) under the form of solid materials, a liquid additive is also provided at the beginning of step a), so as to fluidify the reaction mixture and thus facilitate homogenization of the reaction mixture within the extrusion reactor, and thus improve the reaction between compounds of formula (II) or (II') and (III) or (III'), and optionally a base.

The liquid additive that is added at the beginning of step a) does not chemically interfere with the chemical reaction between compounds (II) or (II') and (III) or (III'), and optionally the base, and thus behaves as a neutral liquid as regards the said chemical reaction.

The liquid additive, when used at step a), may be selected in the group consisting of acetone, water, ethanol, 1-propanol, 2-propanol, ethyl acetate, isopropyl acetate, methanol, methyl ethyl ketone, 1-butanol, 2-butanol, tert-butanol, cyclohexane, pentane, heptane, hexane(s), toluene, methylcyclohexane, methyl tert-butyl ether, diethyl ether, di-isopropyl ether, isooctane, acetonitrile, tetrahydrofurane, 2-methyl tetrahydrofurane, xylenes, dimethylsulfoxide, sulfo lane, N-methylpyrrolidinone, acetic acid, ethylene glycol, dichloromethane, dichloroethane, chloroform, dimethylformamide, pyridine, dimethylacetate, dioxane, dimethoxyethane, glycerol or any other liquid that reduces the viscosity of the reaction mixture. The liquid additive can also be a mixture of two or more of the liquid listed above.

The amount of liquid additive that is added at the beginning of step a) of the continuous synthesis method described herein may be easily determined by the one skilled in the art. The appropriate amount of liquid additive shall sufficiently fluidify the reaction mixture, in general the powder reaction mixture, whereby a reaction mixture paste is formed that will be easily homogenized when worked in the extrusion reactor device. Illustrative embodiments of appropriate amounts of a liquid additive are given in the examples herein.

In some embodiments, the liquid additive is added at an amount ranging from 0.05 mL per gram and 1.0 mL/gram of the solids consisting of (1) the compound of formula (II) or (II'), (2) the compound of formula (III) or (III') and (3) optionally the base, e.g. the carbonate, such as ranging from 0.08 mL/g to 0.3 mL/g, or such as ranging from 0.1 mL/g to 0.2 mL/g.

It shall be understood that the liquid additive which is used at step a) does not consist of a solvent.

As used herein, a "solvent" is a product which solubilizes completely the reagents and does not directly contributes to a chemical reaction. Illustratively, the base which is used in the continuous synthesis method described herein is not a solvent, but instead a reactant compound since the base generates the deprotonation of compound (III) or (III') to favorise its reaction with compound (II).

Otherwise said, the said liquid additive does not dissolve completely the reagents used at step a) and thus does not dissolve the compound of formula (II) or (II'), the compound of formula (III) or (III'), and the base when the latter is present.

It flows that the main effect of the liquid additive is to decrease the viscosity of a reaction mixture that would only comprise the compound of formula (II) or (II'), the compound of formula (III) or (III'), and the base when the latter is present.

In another aspect of the present invention, compounds of formula (I) or (I') may be obtained by reacting two compounds wherein each of two reactants comprise a plurality of amino acid units. Illustratively, according to this other aspect of the invention, two tripeptides may be reacted together so as to form a compound of formula (I) or (I') comprising six amino acid units.

In yet another aspect of the present invention, compounds of formula (I) or (I') may be obtained by reacting three compounds wherein each of two reactants; i.e. the compounds (II) and (III), comprise a plurality of amino acid units, and wherein the third reactant is a base. Illustratively, according to this other aspect of the invention, two tripeptides may be reacted together so as to form a compound of formula (I) or (I') comprising six amino acid units.

The present invention is further described, without in any way being limited to, the examples below.

EXAMPLES

Example 1: General Method of Continuous and Solvent-Free Peptide Synthesis by Reactive Extrusion at Controlled Temperatures Considering the application of reactive extrusion to peptide synthesis, we decided to study the capacity of a co-rotating twin-screw extruder (MC15 micro-compounder, Xplore®) to produce the dipeptide Boc-Trp-Gly-OMe by reacting Boc-Trp-OSu with HCl·H-Gly-OMe and $NaHCO_3$ in the absence of solvent. Yet, the reaction mixture could not be extruded due to the absence of a melted phase preventing proper rotation of the screws. Heating the extrusion barrel at 100° C. did not solve the problem. In order to improve the flowing of the reaction mixture within the extruder barrel, various liquid additives were screened, leading to the identification of acetone as the best liquid additive. Then, Boc-Trp-OSu (1.0 eq.), HCl·H-Gly-OMe (1.1 eq.) and $NaHCO_3$ (1.2 eq.) were poured together with acetone ($\eta$=0.15 mL/g) ($\eta$ is defined as the ratio between the volume of liquid (in mL) divided by the total mass of solids (in gram)) into the extruder operated at 40° C., while the screw speed was fixed at 50 rpm. After 5 minutes of mixing with recirculation of the reaction mixture, the extrudate was quenched and analysed by HPLC, indicating a conversion of 73% (Table 1, entry 1). Increasing the screw speed to 150 rpm and the temperature up to 70° C. had a positive effect on the conversion (Table 1, entries 2 and 3). Conversion reached 93% when the barrel was heated at 100° C., yet leading to partial hydrolysis of Boc-Trp-OSu into Boc-Trp-OH (Table 1, entry 4). When the reaction mixture was recirculated for 10 minutes at 40° C. and 150 rpm, complete conversion of Boc-Trp-OSu was obtained with no traces of Boc-Trp-OH resulting from Boc-Trp-OSu hydrolysis.

TABLE 1

Influence of temperature, mixing time and screw speed on the production of Boc-Trp-Gly-OMe.

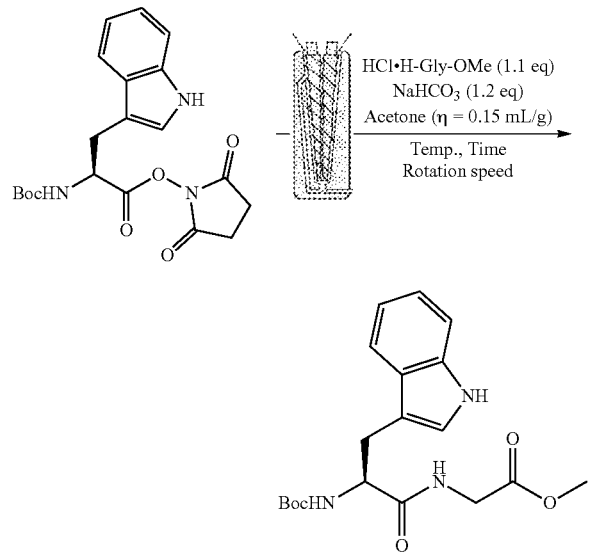

| Entry | Temp. (° C.) | Mixing time (min) | Screw speed (rpm) | Conversion (%)[a] | Hydrolysis (%) |
|---|---|---|---|---|---|
| 1 | 40 | 5 | 50 | 73 | <1 |
| 2 | 40 | 5 | 150 | 85 | <1 |
| 3 | 70 | 5 | 150 | 87 | <1 |
| 4 | 100 | 5 | 150 | 93 | 7 |
| 5 | 40 | 10 | 150 | >99[b] | <1 |

[a]Determined by HPLC.
[b]Boc-Trp-Gly-OMe was produced in 85% yield with >99% enantiomeric excess.

After classical work-up of the extrudate, Boc-Trp-Gly-OMe was produced in 85% yield with complete retention of the enantiomeric excess (>99% ee; Table 1, entry 5).

Example 2: Synthesis of Various Enantiomerically Pure Dipeptides and Tripeptides These optimised reaction conditions were then applied to the synthesis of Boc-Trp-Phe-OMe that could be isolated in 61% yield and >99% diastereomeric excess (Table 2, entry 1). To our delight, Boc-Asp(OBzl)-OSu was even more reactive than Boc-Trp-OSu as Boc-Asp(OBzl)-Phe-OMe could be obtained without the need to recirculate the reaction mixture in the extruder. The 1.5 minute residence time in the extrusion barrel was sufficient to get full conversion of Boc-Asp(OBzl)-OSu, leading to Boc-Asp(OBzl)-Phe-OMe in 92% yield and >99% de (Table 2, entry 2). After Boc removal by solvent-free gaseous HCl treatment, HCl·H-Trp-Gly-OMe and HCl·H-Trp-Phe-OMe were reacted with Boc-Asp(OBzl)-OSu in the extruder. Corresponding Boc-Asp(OBzl)-Trp-Gly-OMe and Boc-Asp(OBzl)-Trp-Phe-OMe tripeptides were produced in 86% and 89% yield and excellent purity (96% and 94% respectively; Table 2, entries 3 & 4).

TABLE 2

Synthesis of various di- and tripeptides by reactive extrusion.

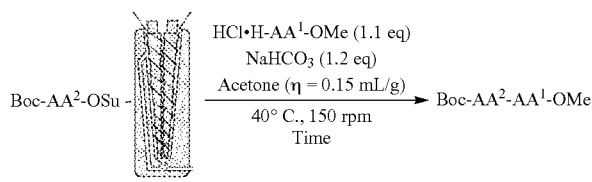

| Entry | AA² | AA¹ | Mixing time (min) | Yield (%) | Purity (%) | Boc-AA²-AA¹-OMe |
|---|---|---|---|---|---|---|
| 1 | Trp | Phe | 10 | 61 | >99[a] | Trp-Phe |
| 2 | Asp(OBzl) | Phe | 1.5[b] | 92 | >99[a] | Asp(OBzl)-Phe |
| 3 | Asp(OBzl) | Trp-Gly | 10 | 86 | 96[c] | Asp(OBzl)-Trp-Gly |
| 4 | Asp(OBzl) | Trp-Phe | 10 | 89 | 94[c] | Asp(OBzl)-Trp-Phe |

[a]>99% de determined by HPLC.
[b]Reaction mixture was extruded without recirculation. Residence time of 1.5 minute.
[c]Purity determined by HPLC.

Example 3: Comparative Analysis of Peptide Synthesis in Solution and by Reactive Extrusion In order to compare the efficiency of the reactive extrusion process with syntheses in a ball-mill and in solution, we calculated the space time yields (STY) of each of these processes. Space time yield is defined as the amount of final product per volume of the reactor per time of reaction (expressed in g cm$^3$ day$^{-1}$) and therefore is a very useful tool to assess process intensification. For the two dipeptides that were compared, the STY was much higher than for ball-mill and solution synthesis, by more than 3 orders of magnitude when comparing to solution specifically (Table 3, entries 1 & 3). In the meantime, the amount of waste produced was drastically reduced when compared to synthesis in ball-mill or in solution. While the E-factor ranged from 0.9 to 1.2 when using reactive extrusion, this metric was always higher for the ball-mill synthesis and from 12 to 33 more times higher in solution (Table 3).

TABLE 3

Space time yield (STY) and E-factor of reactive extrusion, ball-mill and solution synthesis.

| Entry | Boc-aa$^2$-aa$^1$-OMe | STY[a] | | | E-factor | | |
|---|---|---|---|---|---|---|---|
| | | Extruder | Ball-mill | Solution | Extruder | Ball-mill | Solution |
| 1 | Trp-Gly | 48.0 | 2.6 | 0.04 | 1.2 | 1.3 | 39 |
| 2 | Asp(OBzl)-Phe | 376.5 | 2.2 | 0.03–0.23 | 0.9 | 1.8 | 11–30 |

[a]STY expressed in g cm$^3$ day$^{-1}$.

Example 4: Synthesis of Boc(L)-Trp-Gly-OMe (CAS 57769-48-9)

Boc-(L)-Trp-OSu (6.27 g, 15.617 mmol, 1.0 eq), NaHCO$_3$ (1.57 g, 18.740 mmol, 1.2 eq), HCl·H-Gly-OMe (2.16 g, 17.179 mmol, 1.1 eq) and reagent grade acetone (1.5 mL, η=0.15 μL/mg, 1.3 eq) were introduced in a beaker and mixed up with a spatula for 30 seconds. The mixture was slowly poured into the extruder that was heated at 40° C., the speed screw being set at 150 rpm and the output valve turned towards the recirculation pipe. After 10 minutes of recirculation, the valve was opened and a brown paste was recovered. After 24 h drying under reduced pressure over P$_2$O$_5$, the resulting brown solid (m=6.64 g, containing m=4.36 g of pure peptide if 100% yield) was dissolved in EtOAc (200 mL) and washed twice with 1M aqueous HCl solution (2×75 mL) and twice with 1M aqueous NaOH solution (2×75 mL). The organic phase was dried over MgSO$_4$, filtered and concentrated under reduced pressure to afford the desired product as a pale yellow solid (m=3.72 g, 85% yield, STY: 48.02 g·cm$^{-3}$·day$^{-1}$).

Details of STY Calculations
Estimated total mass of peptide: n(limitating reactant)×yield×M(peptide)=15.617×0.85×375.43=5.0 g
Reaction time: 10 minutes=6.94×10$^{-3}$ day
Volume of reactor: 15 mL
STY: 5.00/(15×6.94×10$^{-3}$)=48.02 g·cm$^{-3}$·day$^{-1}$
Details of E-Factor Calculations
Boc-(L)-Trp-OSu: 6.27 g
HCl·H-Gly-OMe: 2.16 g
NaHCO$_3$: 1.57 g
Acetone: 1.5 mL×0.784 g·mL$^{-1}$=1.18 g
Total amount of reactants: 6.27+2.16+1.57+1.18=11.18 g
E-factor=(11.18/5.00)−1=1.24

$^1$H NMR (300 MHz, CDCl$_3$) δ (ppm) 8.32 (s, 1H), 7.62 (d, J=7.8 Hz, 1H), 7.35 (d, J=8.0 Hz, 1H), 7.18-7.07 (3H), 6.40 (t, J=4.9 Hz, 1H), 5.17 (br s, 1H), 4.48 (br s, 1H), 3.98-3.83 (2H), 3.67 (s, 3H), 3.42-3.17 (2H), 1.41 (s, 9H); $^{13}$C (101 MHz, CDCl$_3$) δ (ppm) 172.4, 170.3, 155.9, 136.6, 127.9, 123.7, 122.6, 120.0, 119.1, 111.6, 110.7, 80.6, 55.5, 52.7, 41.6, 28.6; MS (ESI): m/z=398.2 [M+Na]$^+$ Enantiomeric excess was determined by HPLC analysis (Chiralpak IE, heptane/ethanol: 70/30), Flow rate=1 mL/min, T=26° C., λ=220.4 and 230.4 nm, t$_r$=7.40 min (D) and t$_r$=8.34 min (L), >99% ee.

Example 5: Synthesis of Boc-Trp-(L)-Phe-OMe (CAS 72156-62-8)

Boc-(L)-Trp-OSu (5.43 g, 13.523 mmol, 1.0 eq), NaHCO$_3$ (1.36 g, 16.228 mmol, 1.2 eq), HCl·H-(L)-Phe-OMe (3.21 g, 14.876 mmol, 1.1 eq) and reagent grade acetone (1.5 mL, η=0.15 μL/mg, 1.5 eq) were introduced in a beaker and mixed up with a spatula for 30 seconds. The mixture was slowly poured into the extruder that was heated at 40° C., the speed screw being set at 150 rpm and the output valve turned towards the recirculation pipe. After 10 minutes of recirculation, the valve was opened and a white paste was recovered. After 24 h drying under reduced pressure over P$_2$O$_5$, the resulting white solid (m=4.96 g, containing m=3.44 g of pure peptide if 100% yield) was dissolved in EtOAc (150 mL) and washed once with 1M aqueous HCl solution (50 mL) and twice with 1M aqueous NaOH solution (2×70 mL). The organic phase was dried over MgSO$_4$, filtered and concentrated under reduced pressure to afford the desired product as a white solid (m=2.11 g, 61% yield, STY: 36.98 g·cm$^{-3}$·day$^{-1}$).

Details of STY Calculations
Estimated total mass of peptide: n(limitating reactant)×yield×M(peptide)=13.523×0.61×465.55=3.85 g
Reaction time: 10 minutes=6.94×10$^{-3}$ day
Volume of reactor: 15 mL
STY: 3.85/(15×6.94×10$^{-3}$)=36.98 g·cm$^{-3}$·day$^{-1}$
Details of E-Factor Calculations
Boc-(L)-Trp-OSu: 5.43 g
HCl·H-(L)-Phe-OMe: 3.21 g
NaHCO$_3$: 1.36 g
Acetone: 1.5 mL×0.784 g·mL$^{-1}$=1.18 g
Total amount of reactants: 5.43+3.21+1.36+1.18=11.18 g
Estimated total mass of peptide: 3.85 g
E-factor=(11.18/3.85)−1=1.90

$^1$H NMR (300 MHz, CDCl$_3$) δ (ppm) 8.21 (s, 1H), 7.66 (d, J=7.7 Hz, 1H), 7.35 (d, J=7.9 Hz, 1H), 7.20-7.16 (5H), 7.13 (s, 1H), 6.81 (d, J=6.0 Hz, 2H), 6.24 (br d, J=7.1 Hz, 1H), 5.13-5.04 (1H), 4.73 (br d, J=6.4 Hz, 1H), 4.43 (br s, 1H), 3.61 (s, 3H), 3.41-3.28 (1H), 3.14 (dd, J=14.5, 7.0 Hz, 1H), 2.94 (d, J=5.8 Hz, 2H), 1.42 (s, 9H); $^{13}$C (101 MHz, CDCl$_3$) δ (ppm) 171.5, 136.5, 135.8, 129.4, 128.7, 127.2, 123.5, 122.5, 120.0, 119.1, 111.4, 55.4, 53.4, 52.4, 38.1, 28.5, 25.8; MS (ESI): m/z=488.2 [M+Na]$^+$ Diastereoisomeric excess was determined by HPLC analysis (Chromolith® high resolution RP-18e 50-4.6 mm, H$_2$O/0.1% TFA in CH$_3$CN/0.1% TFA: 0-100%), Flow rate=3 mL/min, T=26° C., λ=214 nm, t$_r$=2.81 min (L,L) and tr=2.90 min (D,L), >99% de.

Example 6: Synthesis of Boc-(L)-Asp(OBzl)-(L)-Phe-OMe (CAS 104413-52-7)

Boc-(L)-Asp(OBzl)-OSu (5.54 g, 13.185 mmol, 1.0 eq), NaHCO$_3$ (1.32 g, 15.822 mmol, 1.2 eq), HCl·H-(L)-Phe-OMe (3.13 g, 14.503 mmol, 1.1 eq) and reagent grade acetone (1.5 mL, η=0.15 μL/mg, 1.5 eq) were introduced in a beaker and mixed up with a spatula for 30 seconds. The mixture was slowly poured into the extruder that was heated at 40° C., the speed screw being set at 150 rpm. After having started to introduce the reagent in the extruder, a white paste started to get out from the extruder (residence time: 1 minute 30 seconds). After 24 h drying under reduced pressure over P$_2$O$_5$, the resulting white solid (m=5.60 g, containing m=3.93 g of pure peptide if 100% yield) was suspended in EtOAc (100 mL) and washed twice with 1M aqueous hydrochloric solution (2×30 mL). The organic phase was dried over MgSO$_4$, filtered and concentrated under reduced pressure to afford the desired product as a white powder (m=3.62 g, 92% yield, STY: 376.51 g·cm$^{-3}$·day$^{-1}$).

Details of STY Calculations
Estimated total mass of peptide: n(limiting reactant)×yield×M(peptide)=13.185×0.92×484.55=5.88 g
Reaction time: 1.5 minute=1.04×10$^{-3}$ day
Volume of reactor: 15 mL
STY: 5.88/(15×1.04×10$^{-3}$)=376.51 g·cm$^{-3}$·day
Details of E-Factor Calculations
Boc-(L)-Asp(OBzl)-OSu: 5.54 g
HCl·H-(L)-Phe-OMe: 3.13 g
NaHCO$_3$: 1.33 g
Acetone: 1.5 mL×0.784 g·mL$^{-1}$=1.18 g
Total amount of reactants: 5.54+3.13+1.33+1.18=11.18 g
Estimated total mass of peptide: 5.88 g
E-factor=(11.18/5.88)−1=0.90

$^1$H NMR (300 MHz, CDCl$_3$) δ (ppm) 7.34-7.24 (8H), 7.13 (d, J=6.5 Hz, 2H), 6.93 (br d, J=7.0 Hz, 1H) 5.64 (d, J=8.0 Hz, 1H), 5.15 (d, J=12.3 Hz, 1H), 5.10 (d, J=12.3 Hz, 1H), 4.81 (dd, J=13.4 Hz, 5.9 Hz, 1H), 4.53 (br s, 1H) 3.68 (s, 3H), 3.10-3.02 (3H), 2.70 (dd, J=17.2 Hz, 6.0 Hz, 1H), 1.42 (s, 9H); $^{13}$C (101 MHz, CDCl$_3$) δ (ppm) 171.9, 171.5, 170.5, 155.5, 135.8, 135.5, 129.4, 128.7, 128.5, 128.4, 127.2, 80.6, 67.0, 53.6, 52.4, 50.6, 37.9, 36.1, 28.3; MS (ESI): m/z=485.2 [M+H]$^+$ Diastereoisomeric excess was determined by HPLC analysis (Chiralpak IC, heptane/ethanol: 90/10), Flow rate=1 mL/min, T=26° C., λ=210.4 and 220.4 nm, t$_r$=14.06 min (D,L) and tr=15.79 min (L,L), >99% de.

Example 7: Synthesis of Boc-(L)-Asp(Bzl)-(L)-Trp-Gly-OMe

Boc-(L)-Asp(OBzl)-OSu (4.87 g, 11.572 mmol, 1.0 eq), NaHCO$_3$ (1.12 g, 13.889 mmol, 1.2 eq), HCl·H-(L)-Trp-(L)-Phe-OMe (3.97 g, 12.729 mmol, 1.1 eq) and reagent grade acetone (1.5 mL, η=0.15 μL/mg, 1.8 eq) were introduced in a beaker and mixed up with a spatula for 30 seconds. The mixture was slowly poured into the extruder that was heated at 40° C., the speed screw being set at 150 rpm and the output valve turned towards the recirculation pipe. After 10 minutes of recirculation, the valve was opened and a brown sticky paste was recovered. After 24 h drying under reduced pressure over P$_2$O$_5$, the resulting brown solid was (m=1.60 g, containing m=1.17 g of pure peptide if 100% yield) dissolved in EtOAc (50 mL), washed twice with 1M aqueous HCl solution (2×25 mL) and twice with 1M aqueous NaOH solution (2×25 mL). The organic phase was dried over MgSO$_4$, filtered and concentrated under reduced pressure to afford the desired product as a brown solid (m=1.00 g, 86% yield, STY: 55.16 g·cm$^{-3}$·day$^{-1}$).

Details of STY Calculations
Estimated total mass of peptide: n(limiting reactant)×yield×M(peptide)=11.572×0.86×580.64=5.75 g
Reaction time: 10 minutes=6.94×10$^{-3}$ day
Volume of reactor: 15 mL
STY: 5.75/(15×6.94×10$^{-3}$)=55.16 g·cm$^{-3}$·day$^{-1}$
Details of E-Factor Calculations
Boc-(L)-Trp-OSu: 4.87 g
HCl·H-Trp-Gly-OMe: 3.97 g
NaHCO$_3$: 1.12 g
Acetone: 1.5 mL×0.784 g·mL$^{-1}$=1.18 g
Total amount of reactants: 4.87+3.97+1.12+1.18=11.18 g
E-factor=(11.18/5.75)−1=0.95

$^1$H NMR (300 MHz, CDCl$_3$) δ (ppm) 8.31 (s, 1H), 7.66 (d, J=7.5 Hz, 1H), 7.35-7.11 (10H), 6.59 (br s, 1H), 5.48 (d, J=7.3 Hz, 1H), 5.09-5.04 (2H), 4.75 (dd, J=13.0, 7.0 Hz, 1H), 4.44 (br d, J=6.8 Hz, 1H), 3.85 (dd, J=18.0, 5.4 Hz, 1H), 3.81 (dd, J=18.0, 5.4 Hz, 1H), 3.64 (s, 3H), 3.38 (dd, J=14.5, 4.9 Hz, 1H), 3.18 (dd, J=14.7, 7.0 Hz, 1H), 2.97 (dd, J=16.7, 4.5 Hz, 1H), 2.77 (dd, J=17.1, 5.9 Hz, 1H), 1.35 (s, 9H); $^{13}$C NMR (101 MHz, CDCl$_3$) δ (ppm) 171.8, 171.6, 171.0, 170.1, 155.8, 136.6, 135.7, 129.0, 128.7, 128.5, 127.9, 123.9, 122.6, 120.1, 119.1, 111.6, 110.4, 81.0, 67.2, 54.2, 52.5, 51.5, 41.5, 36.4, 32.4, 30.1, 28.5, 27.8; HRMS calcd for C$_{30}$H$_{37}$N$_4$O$_8$ [M+H]$^+$: 581.2611; found: 581.2617.

Example 8: Synthesis of Boc-(L)-Asp(Bzl)-(L)-Trp-(L)-Phe-OMe

Boc-(L)-Asp(OBzl)-OSu (4.36 g, 10.381 mmol, 1.0 eq), NaHCO$_3$ (1.05 g, 12.457 mmol, 1.2 eq), HCl·H-(L)-Trp-(L)-Phe-OMe (4.59 g, 11.419 mmol, 1.1 eq) and reagent grade acetone (1.5 mL, η=0.15 μL/mg, 2.0 eq) were introduced in a beaker and mixed up with a spatula for 30 seconds. The mixture was slowly poured into the extruder that was heated at 40° C., the speed screw being set at 150 rpm and the output valve turned towards the recirculation pipe. After 10 minutes of recirculation, the valve was opened and a brown sticky paste was recovered. After 24 h drying under reduced pressure over P$_2$O$_5$, the resulting brown solid (m=1.65 g, containing m=1.24 g of pure peptide if 100% yield) was dissolved in EtOAc (50 mL), washed twice with 1M aqueous HCl solution (2×25 mL) and twice with 1M aqueous NaOH solution (2×25 mL). The organic phase was dried over MgSO$_4$, filtered and concentrated under reduced pressure to afford the desired product as a pale yellow solid (m=1.10 g, 89% yield, STY: 59.52 g·cm$^{-3}$·day$^{-1}$).

Details of STY Calculations
Estimated total mass of peptide: n(limiting reactant)×yield×M(peptide)=10.381×0.89×670.76=6.20 g
Reaction time: 10 minutes=6.94×10$^{-3}$ day
Volume of reactor: 15 mL
STY: 6.20/(15×6.94×10$^{-3}$)=59.52 g·cm$^{-3}$·day$^{-1}$
Details of E-Factor Calculations
Boc-(L)-Trp-OSu: 4.36 g
HCl·H-Trp-Phe-OMe: 4.59 g NaHCO$_3$: 1.05 g
Acetone: 1.5 mL×0.784 g·mL$^{-1}$=1.18 g
Total amount of reactants: 4.36+4.59+1.05+1.18=11.18 g
E-factor=(11.18/6.20)−1=0.80

$^1$H NMR (300 MHz, CDCl$_3$) δ (ppm) 8.18 (s, 1H), 7.71 (d, J=7.7 Hz, 1H), 7.33-6.84 (15H), 6.32 (d, J=6.9 Hz, 1H), 5.54 (d, J=7.8 Hz, 1H), 5.04 (s, 2H), 4.70 (br s, 2H), 4.47 (br s, 1H), 3.60 (s, 3H), 3.33 (dd, J=14.4, 4.6 Hz, 1H), 3.10 (dd, J=14.6, 7.5 Hz, 1H), 3.02-2.85 (3H), 2.75 (dd, J=17.1, 6.0 Hz, 1H), 1.41 (s, 9H); $^{13}$C NMR (101 MHz, CDCl$_3$) δ (ppm) 171.7, 171.4, 170.7, 155.5, 136.4, 135.9, 135.5, 129.2, 128.7, 128.6, 128.5, 128.3, 127.1, 122.4, 119.9, 111.3, 110.4, 80.7, 67.0, 54.0, 53.5, 52.3, 51.0, 37.8, 36.3, 28.3, 27.9; HRMS calcd for C$_{37}$H$_{43}$N$_4$O$_8$ [M+H]$^+$: 671.3081; found: 671.3078.

Example 9: Synthesis of Boc-(L)-Trp-Gly-OH

Boc-(L)-Trp-OSu (6.74 g, 16.792 mmol, 1.0 eq), H-Gly-ONa (3.26 g, 33.585 mmol, 2.0 eq) and distilled water (1.5 mL, η=0.15 μL/mg, 5.0 eq) were introduced in a beaker and mixed up with a spatula for 30 seconds. The mixture was slowly poured into the extruder that was heated at 40° C., the speed screw being set at 150 rpm and the output valve turned towards the recirculation pipe. After 3 minutes of recirculation, the valve was opened and a white paste was recovered. After 24 h drying under reduced pressure over P$_2$O$_5$, the resulting white solid (m=7.05 g, containing m=4.03 g of pure peptide if 100% yield) was dissolved in distilled water (100 mL), acidified with 1M aqueous hydrochloride solution until pH=3. The resulting precipitate was filtered and washed twice with deionized water and dry under reduced pressure over P$_2$O$_5$ to afford the desired product as a white powder (m=3.71 g, 92% yield, STY: 177.14 g·cm$^{-3}$·day$^{-1}$).

Details of STY Calculations
Estimated total mass of peptide: n(limiting reactant)×yield×M(peptide)=16.792×0.92×361.4=5.58 g
Reaction time: 3 minutes=2.1×10$^{-3}$ day
Volume of reactor: 15 mL
STY: 5.58/(15×2.0×10$^{-3}$)=177.14 g·cm$^{-3}$·day
Details of E-Factor Calculations
Boc-(L)-Trp-OSu: 6.74 g
H-Gly-ONa: 3.26 g
water: 1.5 mL×1 g·mL$^{-1}$=1.5 g
Total amount of reactants: 6.74+3.26+1.50=11.50 g
Estimated total mass of peptide: 5.58 g
E-factor=(11.50/5.58)−1=1.06

$^1$H NMR (300 MHz, DMSO-d6) δ (ppm) 10.79 (s, 1H), 8.22 (br s, 1H), 7.60 (d, J=7.6 Hz, 1H), 7.32 (d, J=7.7 Hz, 1H), 7.14 (s, 1H), 7.06 (t, J=7.6 Hz, 1H), 6.97 (t, J=7.1 Hz, 1H), 6.76 (d, J=8.1 Hz, 1H), 4.23 (br s, 1H), 3.85-3.80 (m, 2H), 3.12 (d, J=11.3 Hz, 1H), 2.93-2.85 (m, 1H), 1.30 (s, 9H); $^{13}$C NMR (101 MHz, DMSO-d6) δ (ppm) 172.7, 171.5, 155.2, 136.0, 127.7, 124.2, 121.1, 118.7, 118.4, 111.5, 110.6, 77.9, 55.0, 28.4, 28.1; MS (ESI): m/z=362.2 [M+H]+

Enantiomeric excess was determined by HPLC analysis (Chiralpak ID-H, heptane/ethanol+0.1% TFA: 60/40), Flow rate=1 mL/min, T=26° C., λ=220.4 and 254.4 nm, t$_r$=5.93 min (D) and t$_r$=7.38 min (L), >99% ee.

Example 10: Synthesis of Boc-(L)-Trp-D-Phe-OMe [90983-25-8]

Boc-(L)-Trp-OSu (5.43 g, 13.5 mmol), NaHCO$_3$ (1.36 g, 16.2 mmol, 1.2 eq), HCl·H-(D)-Phe-OMe (3.21 g, 14.9 mmol, 1.1 eq) and reagent grade acetone (1.5 mL, η=0.15 μL/mg, 1.5 eq) were introduced in a beaker and mixed up with a spatula for 30 seconds. The mixture was slowly poured into the extruder that was heated at 40° C., the speed screw being set at 150 rpm and the output valve turned towards the recirculation pipe. After 10 min of recirculation, the valve was opened and a white paste was recovered. After 24 h drying under reduced pressure over P$_2$O$_5$, the resulting white solid (m=6.40 g, containing m=4.44 g of pure peptide if 100% yield) was dissolved in EtOAc (50 mL) and washed with 1M aqueous HCl solution (2×20 mL), with 1M aqueous NaOH solution (2×20 mL) and brine (1×20 mL). The organic phase was dried over MgSO$_4$, filtered and concentrated under reduced pressure to afford 2.99 g of the desired product as a white solid (67% yield, E-factor: 1.65, STY: 40.51 g·cm$^{-3}$·day$^{-1}$).

Details of STY Calculations
Estimated total mass of peptide: n(limiting reactant)×yield×M(peptide)=4.22 g
Reaction time: 10 min=6.94×10$^{-3}$ day
Volume of reactor: 15 mL
STY: 40.51 g·cm$^{-3}$·day$^{-1}$
Details of E-Factor Calculations
Amount of final product: 4.22 g
Mass of acetone: 1.5 mL×0.784=1.18 g
Total mass of reagents=5.43+1.36+3.21+1.18=11.18 g
E-factor=(11.18−4.22)/4.22=1.65

$^1$H NMR (400 MHz, CDCl$_3$) δ (ppm) 8.04 (s, 1H), 7.65 (d, J=7.8 Hz, 1H), 7.36 (d, J=8.1 Hz, 1H), 7.24-7.11 (5H), 6.96 (d, J=1.8 Hz, 1H), 6.84-6.78 (2H), 6.23 (d, J=7.9 Hz, 1H), 5.07 (br s, 1H), 4.78 (dd, J=13.1, 5.5 Hz, 1H), 4.46 (br s, 1H), 3.61 (s, 3H), 3.28 (dd, J=11.2, 5.6 Hz, 1H), 3.16 (dd, J=14.3, 7.4 Hz, 1H), 2.95 (dd, J=13.8, 5.5 Hz, 1H), 2.79 (dd, J=13.3, 4.7 Hz, 1H), 1.40 (s, 9H); $^{13}$C NMR (101 MHz, CDCl$_3$) δ (ppm) 171.7, 171.6, 155.6, 136.4, 135.7, 129.3, 128.8, 127.3, 123.3, 122.5, 119.9, 119.1, 111.5, 110.7, 80.3, 55.3, 53.2, 52.4, 37.9, 29.9, 28.5; LCMS (ESI): m/z=488.2 [M+Na]$^+$; m.p.=149-150° C.

Example 11: Synthesis of Boc-(L)-Trp-β-Ala-OMe

Boc-(L)-Trp-OSu (6.12 g, 15.25 mmol), NaHCO$_3$ (1.54 g, 18.3 mmol, 1.2 eq), HCl·H-ß-Ala-OMe (2.34 g, 16.8 mmol, 1.1 eq) and reagent grade acetone (1.5 mL, η=0.15 μL/mg, 1.3 eq) were introduced in a beaker and mixed up with a spatula for 30 seconds. The mixture was slowly poured into the extruder that was heated at 40° C., the speed screw being set at 150 rpm and the output valve turned towards the recirculation pipe. After 10 min of recirculation, the valve was opened and a white paste was recovered. After 24 h drying under reduced pressure over P$_2$O$_5$, the resulting white solid (m=6.31 g, containing m=4.18 g of pure peptide if 100% yield) was dissolved in EtOAc (50 mL) and washed with 1M aqueous HCl solution (2×20 mL), with 1M aqueous NaOH solution (2×20 mL) and brine (1×20 mL). The organic phase was dried over MgSO$_4$, filtered and concentrated under reduced pressure to afford the desired product as a yellow solid (m=3.74 g, 90% yield, E-factor: 1.10, STY: 51.04 g·cm$^{-3}$·day$^{-1}$).

Details of STY Calculations
Estimated total mass of peptide: n(limiting reactant)×yield×M(peptide)=5.32 g
Reaction time: 10 min=6.94×10$^{-3}$ day
Volume of reactor: 15 mL
STY: 51.04 g·cm$^{-3}$·day$^{-1}$
Details of E-Factor Calculations Amount of final product: 5.32 g
Mass of acetone: 1.5 mL×0.784=1.18 g
Total mass of reagents=6.12+1.54+2.34+1.18=11.18 g
E-factor=(11.18−5.32)/5.32=1.10

$^1$H NMR (400 MHz, CDCl$_3$) δ (ppm) 8.50 (s, 1H), 7.62 (d, J=7.9 Hz, 1H), 7.33 (d, J=8.1 Hz, 1H), 7.17 (m, 1H), 7.10 (m, 1H), 7.00 (s, 1H), 6.26 (br s, 1H), 5.22 (br s, 1H), 4.38 (br s, 1H), 3.56 (s, 3H), 3.40 (m, 1H), 3.34-3.22 (2H), 3.14 (dd, J=14.3, 7.6 Hz, 1H), 2.37-2.15 (2H), 1.42 (s, 9H); $^{13}$C NMR (101 MHz, CDCl$_3$) δ (ppm) 172.5, 171.8, 155.4, 136.3, 127.4, 123.1, 122.2, 119.7, 118.8, 111.3, 110.6, 80.1, 55.4, 51.7, 34.7, 33.5, 29.8, 28.6, 28.3; HRMS (ESI): calcd for C$_{20}$H$_{27}$N$_3$O$_5$Na=412.1848 [M+Na]$^+$; found=412.1859; m.p.=48-49° C.

Example 12: Synthesis of Boc-Asp(OBzl)-D-Phe-OMe [1516893-20-1]

Boc-(L)-Asp(OBn)-OSu (5.54 g, 13.2 mmol), NaHCO$_3$ (1.33 g, 15.8 mmol, 1.2 eq), HCl·H-D-Phe-OMe (3.13 g, 14.5 mmol, 1.1 eq) and reagent grade acetone (1.5 mL, η=0.15 μL/mg, 1.5 eq) were introduced in a beaker and mixed up with a spatula for 30 seconds. The mixture was slowly poured into the extruder that was heated at 40° C., the speed screw being set at 150 rpm and the output valve turned towards the recirculation pipe. After 5 min of recirculation, the valve was opened and a white paste was recovered. After 24 h drying under reduced pressure over P$_2$O$_5$, the resulting white solid (m=5.60 g, containing m=3.93 g of pure peptide if 100% yield) was dissolved in EtOAc (50 mL) and washed with 1M aqueous HCl solution (2×20 mL), with 1M aqueous NaOH solution (2×20 mL) and brine (1×20 mL). The organic phase was dried over MgSO$_4$, filtered and concentrated under reduced pressure to afford the desired product as a white solid (m=3.45 g, 88% yield, E-factor: 1.00, STY: 107.58 g·cm$^{-3}$·day$^{-1}$).

Details of STY Calculations
Estimated total mass of peptide: n(limitating reactant)×yield×M(peptide)=5.60 g
Reaction time: 5 min=3.47×10$^{-3}$ day
Volume of reactor: 15 mL
STY: 107.58 g·cm$^{-3}$·day$^{-1}$
Details of E-Factor Calculations
Amount of final product: 5.60 g
Mass of acetone: 1.5 mL×0.784=1.18 g
Total mass of reagents=5.54+1.33+3.13+1.18=11.18 g
E-factor=(11.18−5.60)/5.60=1.00

$^1$H NMR (400 MHz, CDCl$_3$) δ (ppm) 7.38-7.31 (5H), 7.28-7.19 (3H), 7.11-7.07 (2H), 7.01 (m, 1H), 5.64 (br d, J=8.0 Hz, 1H), 5.12 (d, J=12.3 Hz, 1H), 5.08 (d, J=12.3 Hz, 1H), 4.83 (m, 1H), 4.54 (br s, 1H), 3.69 (s, 3H), 3.15-2.92 (3H), 2.66 (dd, J=17.1, 6.0 Hz, 1H), 1.42 (s, 9H); $^{13}$C NMR (101 MHz, CDCl$_3$) δ (ppm) 171.5, 170.4, 155.6, 135.8, 135.5, 129.3, 128.6, 128.4, 128.3, 127.1, 80.5, 66.9, 53.4, 52.3, 50.5, 38.0, 36.1, 28.3; LCMS (ESI): m/z=507.1 [M+Na]$^+$; m.p.=72-73° C.

Example 13: Synthesis of Boc-Asp(OBzl)-β-Ala-OMe

Boc-(L)-Asp(OBn)-OSu (6.23 g, 14.8 mmol), NaHCO$_3$ (1.49 g, 17.8 mmol, 1.2 eq), HCl·H-ß-Ala-OMe (2.28 g, 16.3 mmol, 1.1 eq) and reagent grade acetone (1.5 mL, η=0.15 μL/mg, 1.4 eq) were introduced in a beaker and mixed up with a spatula for 30 seconds. The mixture was slowly poured into the extruder that was heated at 40° C., the speed screw being set at 150 rpm and the output valve turned towards the recirculation pipe. After 10 min of recirculation, the valve was opened and a white paste was recovered. After 24 h drying under reduced pressure over P$_2$O$_5$, the resulting white solid (m=7.35 g, containing m=4.95 g of pure peptide if 100% yield) was dissolved in EtOAc (50 mL) and washed with 1M aqueous HCl solution (2×20 mL), with 1M aqueous NaOH solution (2×20 mL) and brine (1×20 mL). The organic phase was dried over MgSO$_4$, filtered and concentrated under reduced pressure to afford the desired product as a yellow oil (m=3.77 g, 76% yield, E-factor: 1.43, STY: 44.25 g·cm$^{-3}$·day$^{-1}$).

Details of STY Calculations
Estimated total mass of peptide: n(limitating reactant)×yield×M(peptide)=4.61 g
Reaction time: 10 min=6.94×10$^{-3}$ day
Volume of reactor: 15 mL
STY: 44.25 g·cm$^{-3}$·day$^{-1}$
Details of E-Factor Calculations
Amount of final product: 4.61 g
Mass of acetone: 1.5 mL×0.784=1.18 g
Total mass of reagents=6.23+1.49+2.28+1.18=11.18 g
E-factor=(11.18−4.61)/4.61=1.43

$^1$H NMR (400 MHz, CDCl$_3$) δ (ppm) 7.37-7.29 (5H), 6.94 (br s, 1H), 5.63 (br d, J=7.2 Hz, 1H), 5.13 (d, J=12.3 Hz, 1H), 5.09 (d, J=12.3 Hz, 1H), 4.47 (br s, 1H), 3.68 (s, 3H), 3.50 (dd, J=6.2, 6.1 Hz, 2H), 3.04 (dd, J=17.1, 4.3 Hz, 1H), 2.71 (dd, J=17.1, 5.9 Hz, 1H), 2.50 (t, J=6.1 Hz, 2H), 1.44 (s, 9H); $^{13}$C NMR (101 MHz, CDCl$_3$) δ (ppm) 172.7, 171.7, 170.8, 155.6, 135.5, 128.7, 128.5, 128.3, 80.6, 66.9, 51.9, 50.8, 36.3, 35.1, 33.8, 28.4; HRMS (ESI): calcd for C$_{20}$H$_{29}$N$_2$O$_7$=409.1975 [M+H]$^+$; found=409.1978.

Example 14: Synthesis of Fmoc-Leu-Phe-OMe[1] [827018-96-2]

Fmoc-(L)-Leu-OSu (5.71 g, 12.7 mmol), NaHCO$_3$ (1.28 g, 15.2 mmol, 1.2 eq), HCl·H-(L)-Phe-OMe (3.01 g, 13.95 mmol, 1.1 eq) and reagent grade acetone (1.5 mL, η=0.15 μL/mg, 1.6 eq) were introduced in a beaker and mixed up with a spatula for 30 seconds. The mixture was slowly poured into the extruder that was heated at 40° C., the speed screw being set at 150 rpm and the output valve turned towards the recirculation pipe. After 5 min of recirculation, the valve was opened and a solid was recovered. After 24 h drying under reduced pressure over P$_2$O$_5$, the resulting white solid (m=2.41 g, containing m=1.72 g of pure peptide if 100% yield) was dissolved in EtOAc (30 mL) and washed with 1M aqueous HCl solution (2×15 mL), with 1M aqueous NaOH solution (2×15 mL) and brine (1×20 mL). The organic phase was dried over MgSO$_4$, filtered and concentrated under reduced pressure to afford the desired product as a white solid (m=1.38 g, 81% yield, E-factor: 1.13, STY: 100.93 g·cm$^{-3}$·day$^{-1}$).

Details of STY Calculations
Estimated total mass of peptide: n(limitating reactant)×yield×M(peptide)=5.26 g
Reaction time: 5 min=3.47×10$^{-3}$ day
Volume of reactor: 15 mL
STY: 100.93 g·cm$^{-3}$·day$^{-1}$
Details of E-Factor Calculations
Amount of final product: 5.26 g
Mass of acetone: 1.5 mL×0.784=1.18 g
Total mass of reagents=5.71+1.28+3.01+1.18=11.18 g
E-factor=(11.18−5.26)/5.26=1.13

$^1$H NMR (400 MHz, CDCl$_3$) δ (ppm) 7.77 (d, J=7.5 Hz, 2H), 7.59 (d, J=7.1 Hz, 2H), 7.41 (t, J=7.4 Hz, 2H), 7.32 (t, J=7.2 Hz, 2H), 7.24-7.18 (3H), 7.09-7.07 (2H), 6.40 (br d, J=7.0 Hz, 1H), 5.14 (d, J=8.0 Hz, 1H), 4.85 (dd, J=13.5, 6.0 Hz, 1H), 4.44-4.35 (2H), 4.23-4.19 (2H), 3.72 (s, 3H), 3.18-3.05 (2H), 1.63-1.62 (2H), 1.51-1.47 (m, 1H), 0.91 (br s, 6H); $^{13}$C NMR (101 MHz, CDCl$_3$) δ (ppm) 171.9, 171.8, 156.2, 143.9, 141.4, 135.7, 129.3, 128.6, 127.8, 127.23, 127.19, 125.2, 125.1, 120.1, 67.2, 53.5, 53.3, 52.4, 47.2, 41.5, 38.0, 24.7, 23.0, 22.1; LCMS (ESI): 515.2 [M+H]$^+$; m.p.=138-139° C. (lit=137-140° C.).[1]

Example 15: Synthesis of Fmoc-Leu-Val-OBn[2]
[221174-11-4]

Fmoc-(L)-Leu-OSu (4.65 g, 10.3 mmol), NaHCO$_3$ (1.04 g, 12.4 mmol, 1.2 eq), TsOH·H-(L)-Val-OBn (4.31 g, 11.4 mmol, 1.1 eq) and reagent grade acetone (1.5 mL, η=0.15 μL/mg, 2.0 eq) were introduced in a beaker and mixed up with a spatula for 30 seconds. The mixture was slowly poured into the extruder that was heated at 40° C., the speed screw being set at 150 rpm and the output valve turned towards the recirculation pipe. After 10 min of recirculation, the valve was opened and a white powder was recovered. After 24 h drying under reduced pressure over P$_2$O$_5$, the resulting white solid (m=2.65 g, containing m=1.52 g of pure peptide if 100% yield) was dissolved in EtOAc (30 mL) and washed with 1M aqueous HCl solution (2×15 mL), with 1M aqueous NaOH solution (2×15 mL) and brine (1×20 mL). The organic phase was dried over MgSO$_4$, filtered and concentrated under reduced pressure to afford the desired product as a white solid (m=1.13 g, 75% yield, E-factor: 1.67, STY: 40.08 g·cm$^{-3}$·day$^{-1}$).
Details of STY Calculations
Estimated total mass of peptide: n(limiting reactant)×yield×M(peptide)=4.18 g
Reaction time: 10 min=6.94×10$^{-3}$ day
Volume of reactor: 15 mL
STY: 40.08 g·cm$^{-3}$·day$^{-1}$
Details of E-Factor Calculations
Amount of final product: 4.18 g
Mass of acetone: 1.5 mL×0.784=1.18 g
Total mass of reagents=4.65+1.04+4.31+1.18=11.18 g
E-factor=(11.18−4.18)/4.18=1.67
$^1$H NMR (400 MHz, CDCl$_3$) δ (ppm) 7.76 (d, J=7.5 Hz, 2H), 7.58 (d, J=7.3 Hz, 2H), 7.42-7.24 (9H), 6.54 (br d, J=7.5 Hz, 1H), 5.33 (d, J=7.8 Hz, 1H), 5.20 (d, J=11.7 Hz, 1H), 5.11 (d, J=11.7 Hz, 1H), 4.59 (dd, J=8.8, 4.8 Hz, 1H), 4.46-4.33 (2H), 4.30-4.17 (2H), 2.19 (m, 1H), 1.72-1.47 (3H), 1.00-0.74 (12H); $^{13}$C NMR (101 MHz, CDCl$_3$) δ (ppm) 172.3, 171.6, 156.3, 143.9, 143.8, 141.4, 135.4, 128.7, 128.6, 128.5, 127.8, 127.2, 125.2, 120.1, 67.2, 57.2, 53.6, 47.2, 41.5, 31.4, 24.7, 23.0, 22.2, 19.1, 17.7; LCMS (ESI): 543.2 [M+H]$^+$ Example 16: Synthesis of Fmoc-Leu-Gly-OMe[3]
[1316293-41-0]

Fmoc-(L)-Leu-OSu (6.53 g, 14.5 mmol), NaHCO$_3$ (1.46 g, 17.4 mmol, 1.2 eq), HCl·H-Gly-OMe (2.00 g, 16.0 mmol, 1.1 eq) and reagent grade acetone (1.5 mL, η=0.15 μL/mg, 1.4 eq) were introduced in a beaker and mixed up with a spatula for 30 seconds. The mixture was slowly poured into the extruder that was heated at 40° C., the speed screw being set at 150 rpm and the output valve turned towards the recirculation pipe. After 5 min of recirculation, the valve was opened and a white paste was recovered. After 24 h drying under reduced pressure over P$_2$O$_5$, the resulting white solid (m=3.76 g, containing m=2.57 g of pure peptide if 100% yield) was dissolved in EtOAc (30 mL) and washed with 1M aqueous HCl solution (2×15 mL), with 1M aqueous NaOH solution (2×15 mL) and brine (1×20 mL). The organic phase was dried over MgSO$_4$, filtered and concentrated under reduced pressure to afford the desired product as a white solid (m=2.30 g, 90% yield, E-factor: 1.02, STY: 106.07 g·cm$^{-3}$·day$^{-1}$).
Details of STY Calculations
Estimated total mass of peptide: n(limiting reactant)×yield×M(peptide)=5.52 g
Reaction time: 5 min=3.47×10$^{-3}$ day
Volume of reactor: 15 mL
STY: 106.07 g·cm$^{-3}$·day$^{-1}$
Details of E-Factor Calculations
Amount of final product: 5.52 g
Mass of acetone: 1.5 mL×0.784=1.18 g
Total mass of reagents=6.53+1.46+2.00+1.18=11.18 g
E-factor=(11.18−5.52)/5.52=1.02
$^1$H NMR (400 MHz, CDCl$_3$) δ (ppm) 7.76 (d, J=7.5 Hz, 2H), 7.58 (d, J=7.3 Hz, 2H), 7.39 (t, J=7.4 Hz, 2H), 7.30 (t, J=7.4 Hz, 2H), 6.58 (br s, 1H), 5.26 (d, J=8.1 Hz, 1H), 4.42 (br s, 2H), 4.25-4.19 (2H), 4.03 (br s, 2H), 3.73 (s, 3H), 1.68-1.55 (3H), 0.94-0.86 (6H); $^{13}$C NMR (101 MHz, CDCl$_3$) δ (ppm) 172.7, 170.2, 156.4, 143.9, 143.8, 141.4, 127.8, 127.2, 125.1, 120.1, 67.1, 53.5, 52.5, 47.3, 41.4, 41.3, 24.8, 23.0, 22.0; LCMS (ESI): 425.1 [M+H]$^+$; m.p.=113-118° C.

REFERENCES

1. M. L. Di Gioia, A. Leggio, A. Le Pera, A. Liguori, F. Perri and C. Siciliano, *Eur. J. Org. Chem.*, 2004, 2004, 4437.
2. S. J. Tantry, R. V. R. Rao and V. V. S. Babu, *ARKIVOC* (Gainesville, Fla., U.S.), 2006, 21.
3. K. Narita, K. Matsuhara, J. Itoh, Y. Akiyama, S. Dan, T. Yamori, A. Ito, M. Yoshida and T. Katoh, *Eur. J. Med. Chem.*, 2016, 121, 592.

The invention claimed is:
1. A continuous solvent-free and non-enzymatic method for synthesizing a compound of formula (I):

Ra-POLYPEP-Rc     (I)

wherein:
POLYPEP is a poly-amino acid compound,
Ra means a N-protective group;
Rc means-O-Rd, wherein Rd means a hydrogen atom, a (C1-C24 alkyl) group, a methyl group substituted with one or more phenyl groups, a non-substituted (C6-C10) aryl group, a O-protective group or a —NReRf group wherein Re and Rf groups mean, one independently of each other, a hydrogen atom, a (C1-C24) alkyl group, a methyl group substituted with one or more phenyl groups, a non-substituted (C6-C10 aryl) group or a N-protective group,
which method comprises the steps of:
a) feeding an extrusion reactor with
(1) a compound of formula (II)

Ra-PEPNt-Rg     (II)

wherein;
PEPNt is a mono- or a poly-amino acid compound,
Ra is as defined for the compound of formula (I), and
Rg is a leaving group
and
(2) a compound of formula (III)

H-PEPCt-Rc     (III)

wherein:
PEPCt is a mono- or a poly-amino acid compound, and
Rc is as defined for the compound of formula (I)
in the absence of any solvent,
so that the compound of formula (II) and the compound of formula (III) react together for generating a compound of formula (I), and
b) collecting the compound of formula (I) from the extrusion reactor, wherein:
at least one of the compound of formula (II) and the compound of formula (III) is provided in the form of a solution containing a liquid additive, and the step (a) does not include adding a separate liquid additive, wherein an appropriate viscosity of a mixture of the compound of formula (II) and the compound of formula (III) is reached by the liquid additive contained in the solution, or
both the compound of formula (II) and the compound of formula (III) are provided in solid form, and the step (a) further comprises adding a separate liquid additive to reduce a viscosity of a mixture of the compound of formula (II) and the compound of formula (III).

2. The continuous, solvent-free and non-enzymatic method according to claim 1, for synthesizing a compound of formula (I')

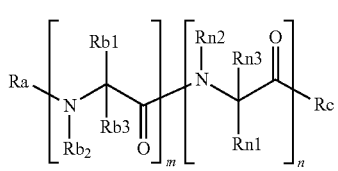

(I')

wherein:
m is an integer of 1 or more,
n is an integer of 1 or more;
Ra means a N-protective group;
each Rb1 represent, one independently from each other, a hydrogen atom, a (C1-C6) alkyl group non-substituted or substituted by a group selected among an aryl group non-substituted or substituted by an —OH group, —OH, —COOH, —CONH2, —SH, —S—(C1-C6 alkyl), —NH2, —NH—C(NH)(NH2), -imidazolyl and indolyl,
Rb2 is selected in the group consisting of a hydrogen atom, an alkyl group, an aryl group or a N-protective group,
each Rb3 represent, one independently from each other, a hydrogen atom, a (C1-C6) alkyl group non-substituted or substituted by a group selected among an aryl group non-substituted or substituted by an —OH group, —OH, —COOH, —CONH2, —SH, —S—(C1-C6 alkyl), —NH2, —NH—C(NH)(NH2), -imidazolyl and indolyl,
or
each paired Rb1 and Rb2, or paired Rb3 and Rb2, one paired Rb1 and Rb2 or one paired Rb2 and Rb3 independently from each other paired Rb1 and Rb2 or paired Rb2 and Rb3, form together with respectively the carbon atom and the nitrogen atom to which they are linked, a heterocyclic ring comprising at least one nitrogen atom, and
each Rn1 represent, one independently from each other, a hydrogen atom, a (C1-C6) alkyl group non-substituted or substituted by a group selected among an aryl group non-substituted or substituted by an —OH group, —OH, —COOH, —CONH2, —SH, —S—(C1-C6 alkyl), —NH2, —NH—C(NH)(NH2), -imidazolyl and indolyl,
Rn2 is selected in the group consisting of a hydrogen atom, an alkyl group or an aryl group, and
each Rn3 represent, one independently from each other, a hydrogen atom, a (C1-C6) alkyl group non-substituted or substituted by a group selected among an aryl group non-substituted or substituted by an —OH group, —OH, —COOH, —CONH2, —SH, —S—(C1-C6 alkyl), —NH2, —NH—C(NH)(NH2), -imidazolyl and indolyl,
or
each paired Rn1 and Rn2, or paired Rn3 and Rn2, one paired Rn1 and Rn2 or one paired Rn3 and Rn2 independently from each other paired Rn1 and Rn2 or paired Rn3 and Rn2, form together with respectively the carbon atom and the nitrogen atom to which they are linked, a heterocyclic ring comprising at least one nitrogen atom
Rc means -O-Rd, wherein Rd means a hydrogen atom, a (C1-C24 alkyl) group, a methyl group substituted with one or more phenyl groups, a non-substituted (C6-C10) aryl group, a O-protective group or a —NReRf group wherein Re and Rf group mean, one independently of each other, a hydrogen atom, a (C1-C24) alkyl group, a methyl group substituted with one or more phenyl groups, a non-substituted (C6-C10 aryl) group or a N-protective group,
which method comprises the steps of:
a) feeding an extrusion reactor with
(1) a compound of formula (II')

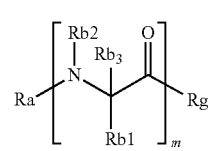

(II')

wherein
m, Ra, Rb1, Rb2 and Rb3 are as defined for the compound of formula (I'), and
Rg is a leaving group
and
(2) a compound of the following formula (III')

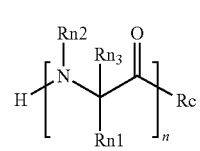

(III')

wherein
n, Rn1, Rn2, Rn3 and Rc are as defined for the compound of formula (I'), in the absence of any solvent, so that the compound of formula (II') and the compound of formula (III') react together for generating a compound of formula (I'), and b) collecting the compound of formula (I') from the extrusion reactor.

3. The continuous method according to claim 2, wherein, when Rb1 and Rb2, or Rb2 and Rb3, form together with respectively the carbon atom and the nitrogen atom to which they are linked, a heterocyclic ring comprising at least one nitrogen atom, the said heterocyclic ring is a pyrrolidinyl group.

4. The continuous method according to claim 2, wherein, when Rn1 and Rn2, or Rn2 and Rn3, form together with respectively the carbon atom and the nitrogen atom to which they are linked, a heterocyclic ring comprising at least one nitrogen atom, the said heterocyclic ring is a pyrrolidinyl group.

5. The method according to claim 2, wherein Rb1 is selected in a group consisting of hydrogen atom, a methyl group, —CH2-CH2-CH2-NH—C(=NH)NH2, —CH2-C(=O)—NH2, —CH2-COOH, —CH2-SH, —(CH2)2-C(=O)—NH2, —(CH2)2-COOH, —CH2-Imidazolyl, —CH(CH3)-CH2-CH3, —CH2-CH(CH3)2, —(CH2)4-NH2, —CH2-CH2-S—CH3, —CH2-Phenyl, —CH2OH, —CH(OH)—CH3, —CH2-indolyl, —CH2-phenyl-OH and isopropyl group [Val], Rb3 is a hydrogen atom and Rb2 is a hydrogen atom.

6. The method according to claim 2, wherein Rn1 is selected in a group consisting of hydrogen atom, a methyl group, —CH2-CH2-CH2-NH—C(=NH)NH2-CH2-C(=O)—NH2, —CH2-COOH, —CH2-SH, —(CH2)2-C(=O)—NH2, —(CH2)2-COOH, —CH2-Imidazolyl, —CH(CH3)-CH2-CH3, —CH2-CH(CH3)2, —(CH2)4-NH2, —CH2-CH2-S—CH3, —CH2-Phenyl, —CH2OH, —CH(OH)—CH3, —CH2-indolyl, —CH2-phenyl-OH and isopropyl group [Val], Rn3 is a hydrogen atom and Rn2 is a hydrogen atom.

7. The method according to claim 2, wherein the functions NH2, NH, COOH, CONH2, OH, SH of the Rb1 group of the compound of formula (I) or (II) and of the Rn1 groups of the compounds of formula (I) or (III) are protected by one or more identical or different N-protective, O-protective or S-protective groups.

8. The method according to claim 1, wherein group —C(O)-Rg of the compound of formula (II) is selected in the group consisting of N-substituted carbamates, pentafluorophenyl hydroxylate, succinimidyl N-hydroxylate, imidazolate, benzimidazolate, benzotriazole N-hydroxylate, azabenzotriazole N-hydroxylate, pyrimidine hydroxylate, triazine hydroxylate, paranitrophenyl hydroxylate, oxime, fluoride, bromide, chloride, carboxylates and carbonates.

9. The method according to claim 1, wherein step a) comprises adding a base.

10. The method according to claim 1, wherein the extrusion reactor is selected among a single screw extrusion reactor and a double screw extrusion reactor.

11. The method according to claim 1, wherein step a) is performed by maintaining the reactants at a constant selected temperature.

12. The method according to claim 1, wherein step a) is performed at a temperature ranging from 30° C. to 100° C.

13. The method according to claim 1, wherein step a) is performed at a temperature ranging from 35° C. to 70° C.

14. The method according to claim 1, wherein the base is selected from the group consisting of a mineral base or an organic base.

15. The method according to claim 14, wherein the base is a carbonate and the said carbonate is selected in the group consisting of sodium hydrogenocarbonate, potassium hydrogenocarbonate, cesium hydrogenocarbonate, sodium carbonate, potassium carbonate and cesium carbonate.

16. The method according to claim 1, wherein, in a compound of formula (I) or (II), Ra is selected, one independently of each other, in the group consisting of tert-butyloxycarbonyl, 9-fluorenylmethyloxycarbonyl, benzyloxycarbonyl and nitro-veratryloxycarbonyl.

17. The method according to claim 1, wherein in a compound of formula (I) or (I'), or (III) or (III'), Re and Rf are selected, one independently of each other, in the group consisting of a hydrogen, a (C1-C24) alkyl group, a methyl group substituted with one or more phenyl groups, a non-substituted (C6-C10 aryl) group, or a N-protective group.

18. The method according to claim 2, wherein m is an integer ranging from 1 to 100.

19. The method according to claim 2, wherein n is an integer ranging from 1 to 100.

* * * * *